(12) United States Patent
Steuer et al.

(10) Patent No.: US 6,681,128 B2
(45) Date of Patent: Jan. 20, 2004

(54) SYSTEM FOR NONINVASIVE HEMATOCRIT MONITORING

(75) Inventors: Robert R. Steuer, Pleasant View, UT (US); David H. Harris, Ogden, UT (US)

(73) Assignee: Hema Metrics, Inc., Kaysville, UT (US)

( * ) Notice: Subject to any disclaimer, the term of this patent is extended or adjusted under 35 U.S.C. 154(b) by 7 days.

(21) Appl. No.: 09/879,192

(22) Filed: Jun. 13, 2001

(65) Prior Publication Data

US 2002/0038079 A1 Mar. 28, 2002

Related U.S. Application Data

(63) Continuation of application No. 09/084,958, filed on May 28, 1998, now Pat. No. 6,266,546, which is a continuation of application No. 08/479,352, filed on Jun. 7, 1995, now Pat. No. 5,803,908, which is a continuation of application No. 08/317,726, filed on Oct. 4, 1994, now Pat. No. 5,499,627, which is a division of application No. 08/011,882, filed on Feb. 1, 1993, now Pat. No. 5,372,136, which is a continuation of application No. 07/598,169, filed on Oct. 16, 1990, now abandoned.

(51) Int. Cl.[7] ................................................. A61B 5/00
(52) U.S. Cl. ........................ 600/322; 600/310; 600/330
(58) Field of Search ................................ 600/309–310, 600/322–323, 476, 473; 356/39–41

(56) References Cited

U.S. PATENT DOCUMENTS

| | | | |
|---|---|---|---|
| 3,638,640 A | | 2/1972 | Shaw |
| 3,880,151 A | | 4/1975 | Nilsson |
| 4,014,321 A | | 3/1977 | March |
| 4,066,361 A | * | 1/1978 | Achter .......................... 356/41 |
| 4,081,372 A | | 3/1978 | Atkin et al. |
| 4,086,915 A | | 5/1978 | Kofsky et al. |

(List continued on next page.)

FOREIGN PATENT DOCUMENTS

| | | |
|---|---|---|
| EP | 0104772 | 4/1984 |
| EP | 0160768 | 11/1985 |
| WO | WO 86/06946 | 12/1986 |
| WO | WO 89/01758 | 3/1989 |

OTHER PUBLICATIONS

J.P. Payne and J.W. Severinghaus, Eds., *Pulse Oximetry*, Chapters 1 and 2 (©1986).

John D. Bower and Thomas G. Coleman, *Circulatory Function During Chronic Hemodialysis*, vol. XV Trans. Amer. Soc. Artif. Int. Organs, 1969, 373–377.

(List continued on next page.)

*Primary Examiner*—Eric F. Winakur
*Assistant Examiner*—Matthew Kremer
(74) *Attorney, Agent, or Firm*—Jacobson Holman PLLC

(57) ABSTRACT

A system determines heamtocrit transcutaneously and noninvasively. Disclosed are a finger clip assembly and an earlobe clip assembly, each including at least a pair of emitters and a photodiode in appropriate alignment to enable operation in either a transmissive mode or a reflectance mode. At least two, and preferably three, predetermined wavelengths of light are assed onto or through body tissues such as the finger, earlobe, or scalp, etc. and the extinction of each wavelength is detected. Mathematical manipulation of the detected values compensates for the effects of body tissue and fluid and determines the hematocrit value. If a fourth wavelength of light is used which is extinguished substantially differently by oxyhemoglobin and reduced hemoglobin and which is not substantially extinguished by plasmas, then the blood oxygen saturation value, independent of hematocrit, maybe determined. It is also disclosed how to detect and analyze multiple wavelengths using a logarithmic DC analysis technique. Then a pulse wave is not required. So this method may be utilized in states of low blood pressure or low blood flow.

8 Claims, 27 Drawing Sheets

U.S. PATENT DOCUMENTS

| | | | |
|---|---|---|---|
| 4,181,610 | A | 1/1980 | Shintani et al. |
| 4,223,680 | A | 9/1980 | Jobsis |
| 4,266,554 | A | 5/1981 | Hamaguri |
| 4,295,470 | A | 10/1981 | Shaw et al. |
| 4,416,285 | A | 11/1983 | Shaw et al. |
| 4,446,871 | A | 5/1984 | Imura |
| 4,623,248 | A * | 11/1986 | Sperinde .................... 600/342 |
| 4,653,498 | A | 3/1987 | New et al. |
| 4,655,225 | A | 4/1987 | Dahne et al. |
| 4,685,464 | A | 8/1987 | Goldberger et al. |
| 4,714,080 | A | 12/1987 | Edgar, Jr. et al. |
| 4,770,179 | A | 9/1988 | New et al. |
| 4,805,623 | A | 2/1989 | Jöbsis |
| 4,819,752 | A | 4/1989 | Zelin |
| 4,824,242 | A | 4/1989 | Frick et al. |
| 4,825,872 | A | 5/1989 | Tan et al. |
| 4,825,879 | A | 5/1989 | Tan et al. |
| 4,832,484 | A | 5/1989 | Aoyagi et al. |
| 4,867,557 | A | 9/1989 | Takatani et al. |
| 4,920,972 | A | 5/1990 | Frank et al. |
| 4,925,299 | A | 5/1990 | Meisberger et al. |
| 5,028,787 | A | 7/1991 | Rosenthal et al. |
| 5,035,243 | A | 7/1991 | Muz |
| 5,054,487 | A | 10/1991 | Clarke |
| 5,057,695 | A | 10/1991 | Hirao et al. |
| 5,058,587 | A | 10/1991 | Kohno et al. |
| 5,059,394 | A | 10/1991 | Phillips et al. |
| 5,066,859 | A * | 11/1991 | Karkar et al. ............... 600/326 |
| 5,092,836 | A | 3/1992 | Polaschegg |
| 5,101,825 | A | 4/1992 | Gravenstein et al. |
| 5,111,817 | A | 5/1992 | Clark et al. |
| 5,158,091 | A | 10/1992 | Butterfield et al. |
| H001114 | H | 12/1992 | Schweitzer et al. |
| 5,193,543 | A | 3/1993 | Yelderman |
| 5,237,999 | A | 8/1993 | Von Berg |
| 5,499,627 | A * | 3/1996 | Steuer et al. ............... 600/322 |

OTHER PUBLICATIONS

Larry Reynolds, C. Johnson, A. Ishimaru, *Diffuse reflectance from a finite blood medium: applications to the modeling of fiber optic catheters*, Sep. 1976, vol. 15, No. 9, Applied Optics, pp. 2059–2067.

R.N. Greenwood, C, Aldridge, L. Goldstein, L.R.I. Baker and W.R. Cattell, *Assessment of arteriovenous fistulae from pressure and thermal dilution studies: clinical experience in forearm fistulae*, Clinical Nephrology, vol. 23, No. 4–1985, pp. 189–197.

R.N. Greenwood, C. Aldridge and W.R. Cattell, *Serial blood water estimations and in–line blood viscometry: the continuous measurement of blood volume during dialysis procedures*, Clinical Science (1984)66, pp. 575–583.

C. Aldridge, R.N. Greenwood, W.R. Cattell and R.V. Barrett, *The assessment of arteriovenous fistulae created for haemodialysis from pressure and thermal dilution measurements*, Journal of Medical Engineering & Technology, vol. 8, No. 3, (May/Jun.), pp. 118–124.

L. Goldstein, L. Pavitt, R.N. Greenwood, C. Aldridge, L.R.I. Baker and W.R. Cattell, *The Assessment of Areteriovenous Fistulae From Pressure and Recirculation Studies*, ProcEDTNA–ERCA (1985) vol. 14., pp. 207–215.

R.N. Greenwood, C. Aldridge, L. Goldstein, L.R.I. Baker and W.R. Cattell, *Assessment of Arteriovenous Fistulas From Pressure and Recirculation Studies: Clinical Experience in 215 Upper Limb Fistulas*, ProcEDTA–ERA(1985), vol. 22, pp. 296–302.

Joseph M. Schmitt, James D. Meindl and Frederick G. Mihm, *An Integrated Circuit–Based Optical Sensor for In Vivo Measurement of Blood Oxygenation*, IEEE Transaction On Biomedical Engineering, vol. BME–33, No. 21, Feb. 1986, pp. 98–107.

Joseph M. Schmitt, Fred G. Mihm and James Meindl, *New Methods for Whole Blood Oximetry*, Annals of Biomedical Engineering, vol. 14, pp. 35–52, 1986.

Mark R. Arnfield, J. Tulip and Malcolm McPhee, *Optical Propagation in Tissue With Anisotropic Scattering*, IEEE Transactions on Biomedical Engineering, vol. 35, No. 5, May 1988, pp. 372–381.

\* cited by examiner

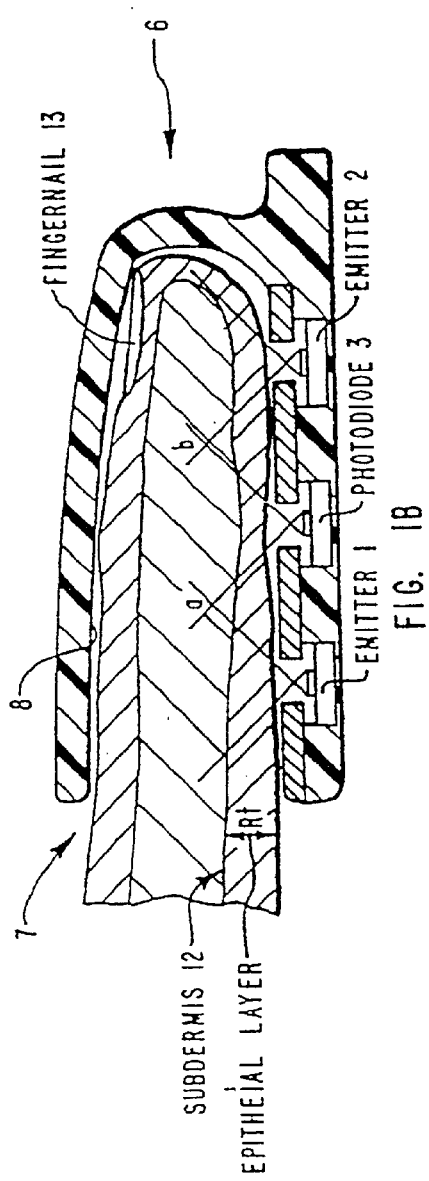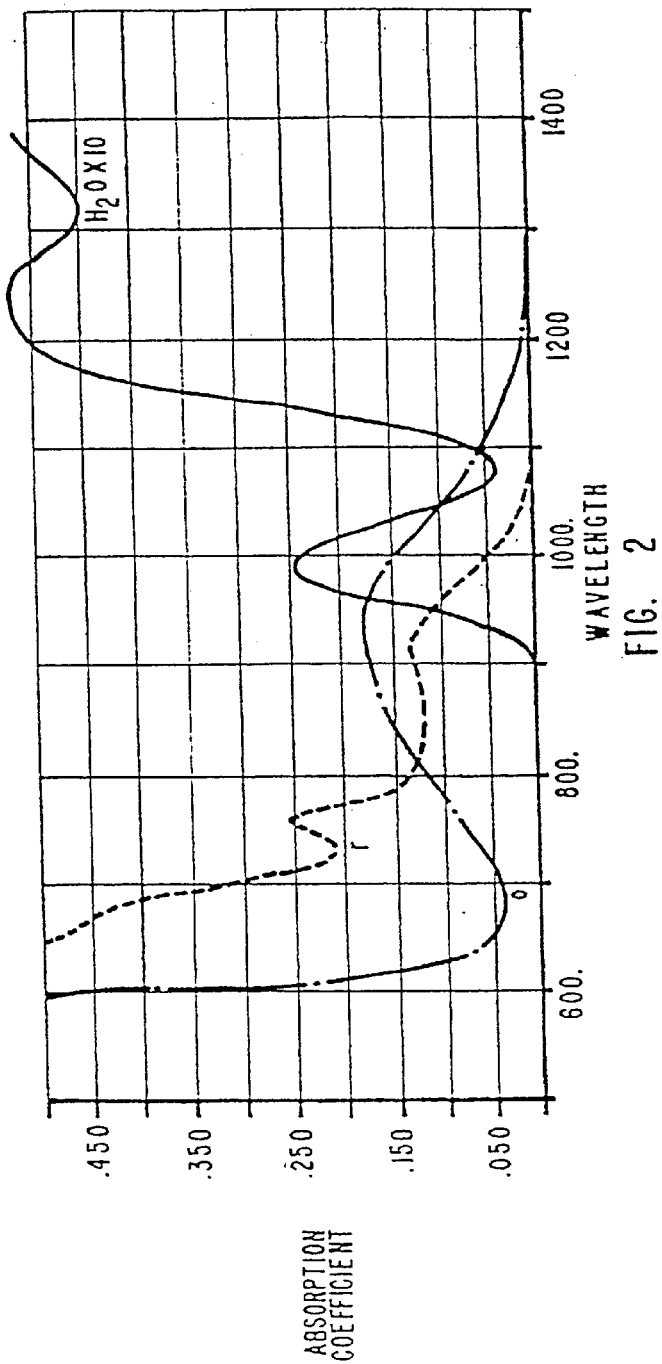

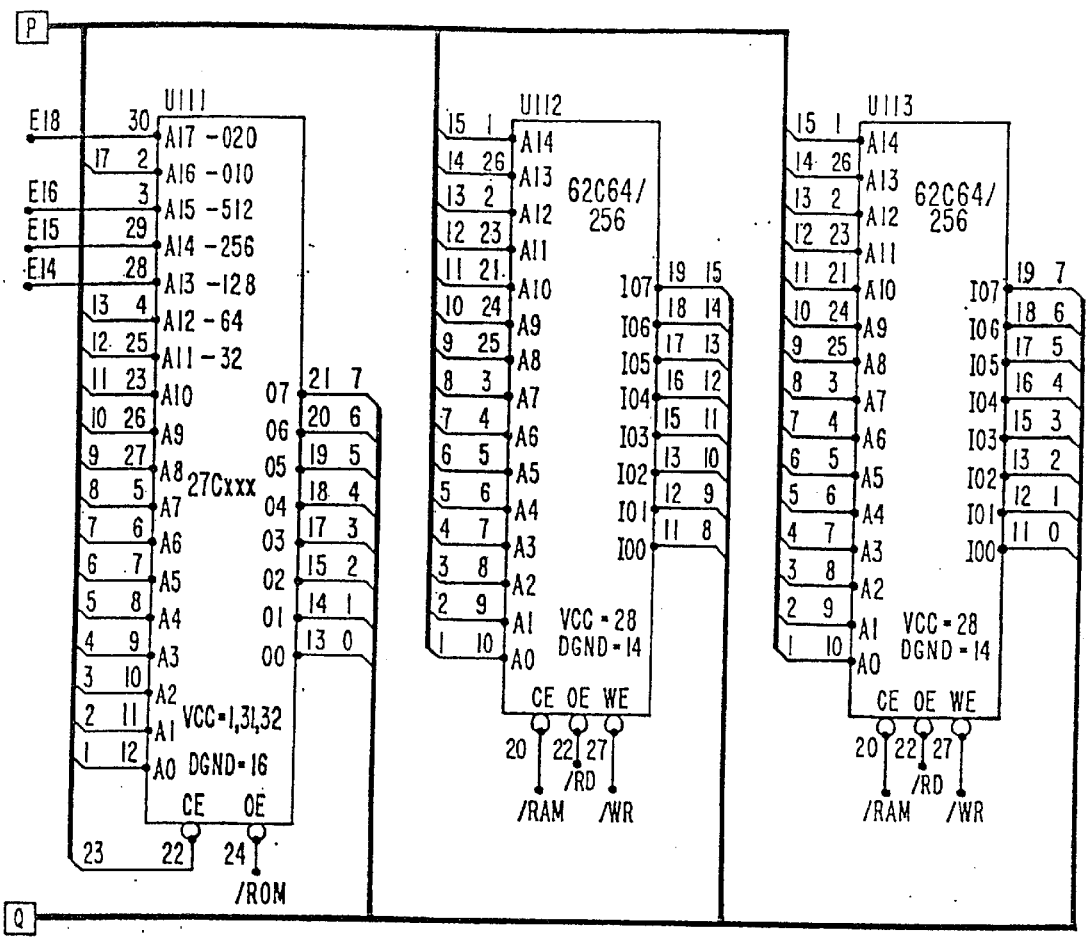
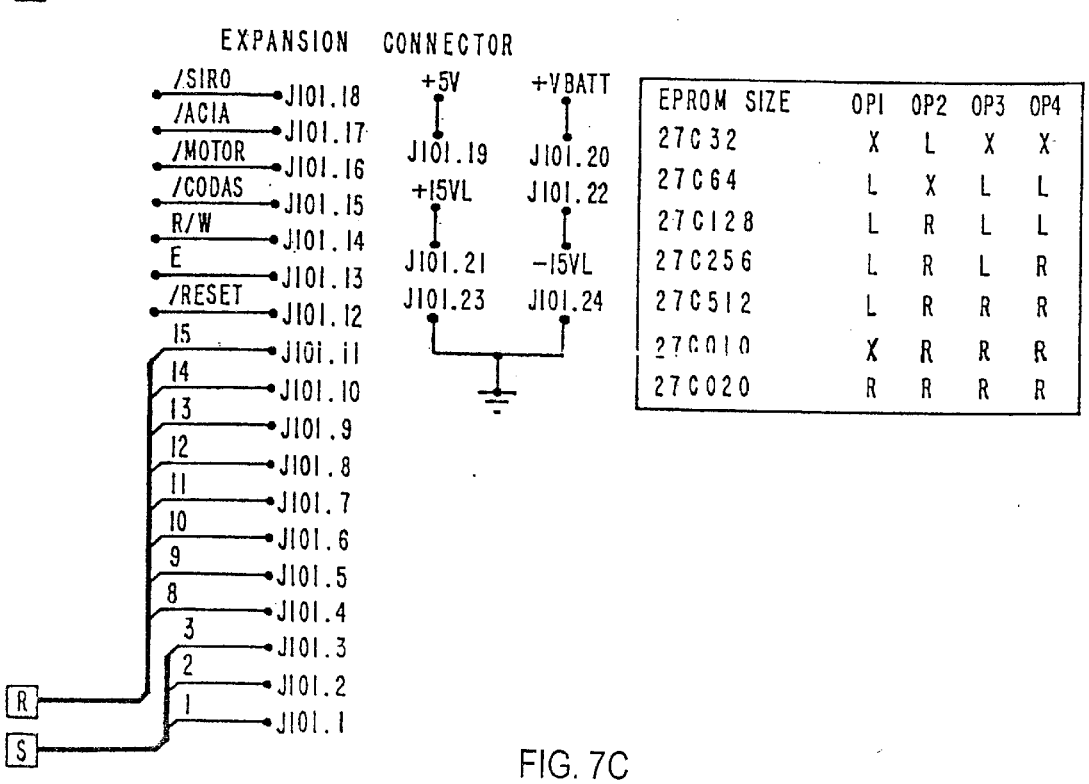
FIG. 7C

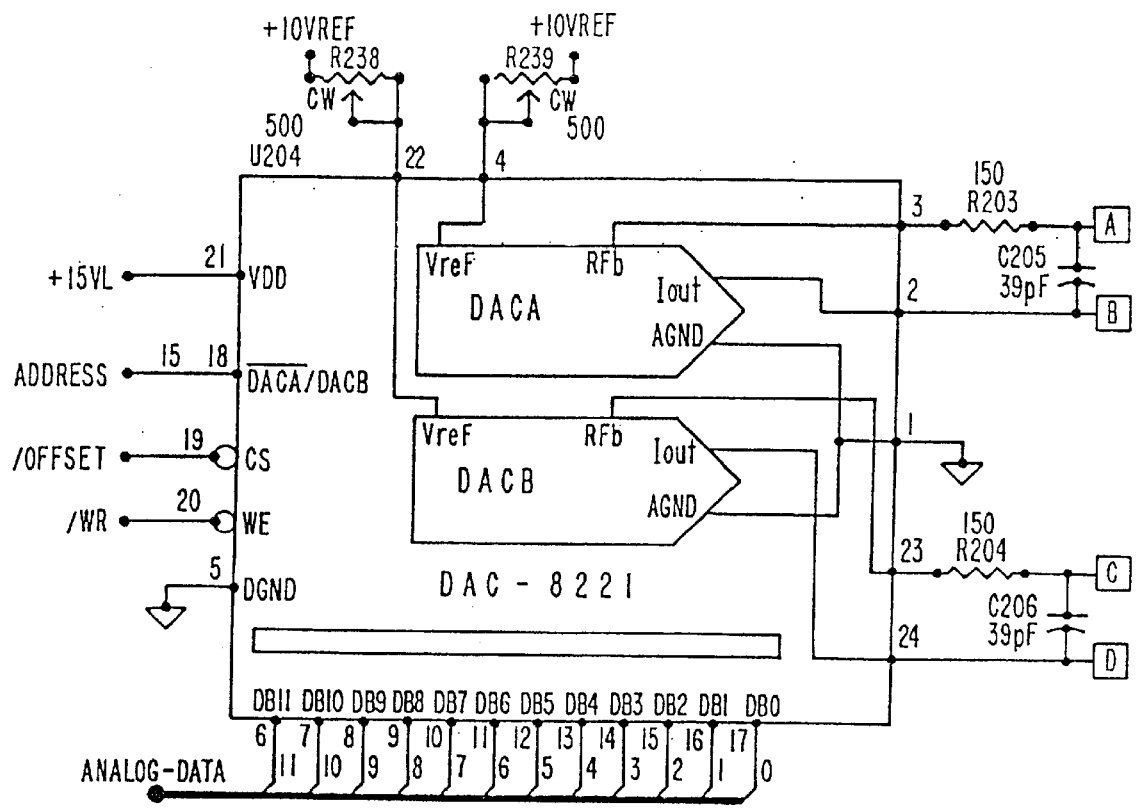
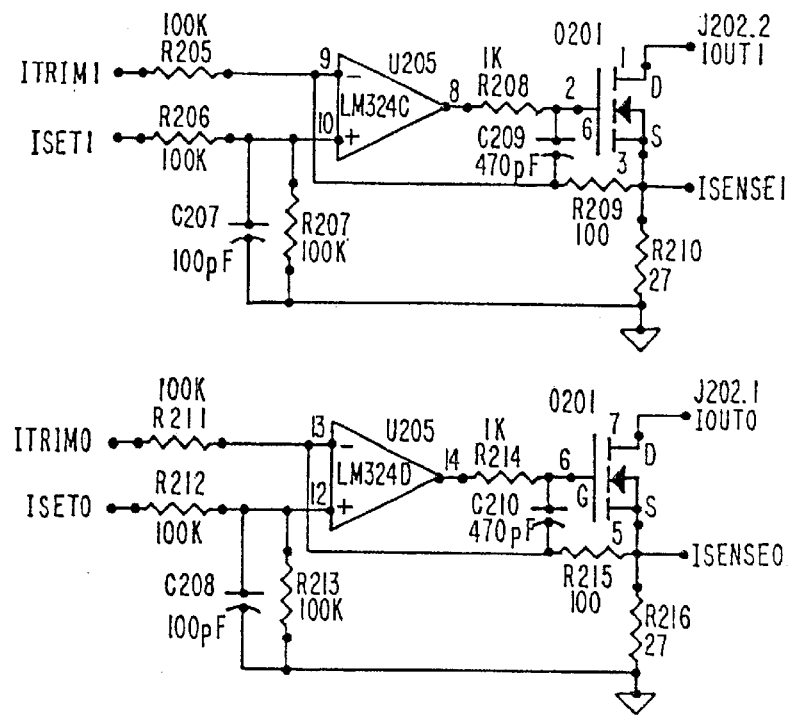
FIG. 8B

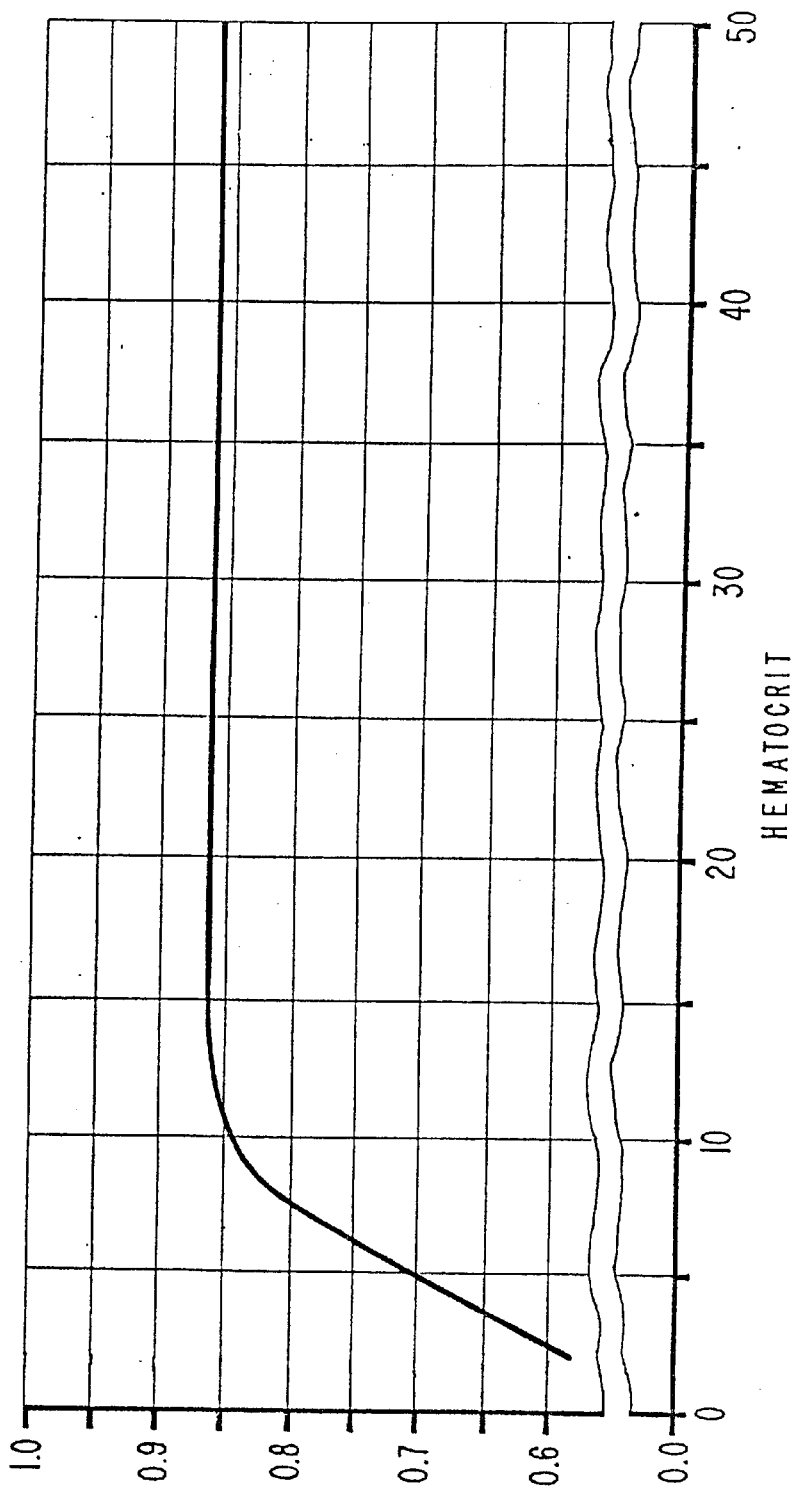
FIG. II

SYSTEM FOR NONINVASIVE HEMATOCRIT MONITORING

This is a continuation of U.S. application Ser. No. 09/084,958, filed May 28, 1998, now U.S. Pat. No. 6,266,546, which is a continuation of U.S. application Ser. No. 08/479,352, filed Jun. 7, 1995, now U.S. Pat. No. 5,803,908, which is a continuation of U.S. application Ser. No. 08/317,726, filed Oct. 4, 1994, now U.S. Pat. No. 5,499,627, which is a divisional of U.S. application Ser. No. 08/011,882, filed Feb. 1, 1993, now U.S. Pat. No. 5,372,136, which is a continuation of U.S. application Ser. No. 07/598,169, filed Oct. 16, 1990 (abandoned).

BACKGROUND

1. The Field of the Invention

This invention relates to systems and methods for noninvasively measuring one or more biologic constituent values. More particularly, the present invention relates to noninvasive spectrophotometric systems and methods for quantitatively and continuously monitoring the hematocrit and other blood parameters of a subject.

2. The Prior Art

Modern medical practice utilizes a number of procedures and indicators to assess a patient's condition. One of these indicators is the patient's hematocrit. Hematocrit (often abbreviated as Hct) is the volume, expressed as a percentage, of the patient's blood which is occupied by red corpuscles (commonly referred to as red blood cells).

Human blood consists principally of liquid plasma (which is comprised of over 90% water with more than 100 other constituents such as proteins, lipids, salts, etc.) and three different corpuscles. The three corpuscles found in blood are red corpuscles, white corpuscles, and platelets.

The chief function of red corpuscles is to carry oxygen from the lungs to the body tissues and carbon dioxide from the tissues to the lungs. This critical life supporting function is made possible by hemoglobin which is the principal active constituent of red corpuscles. In the lungs, hemoglobin rapidly absorbs oxygen to form oxyhemoglobin which gives it a bright scarlet color. As the red corpuscles travel to the tissues, the oxyhemoglobin releases oxygen, i.e., is reduced, and the hemoglobin turns a dark red color.

The oxygen transportation functions of the body rely essentially entirely on the presence of hemoglobin in the red corpuscles. Red corpuscles greatly outnumber other corpuscles being about 700 times greater than the number of white corpuscles in a healthy human subject;

Medical professionals routinely desire to know the hematocrit of a patient. In order to determine hematocrit using any of the techniques available to date, it is necessary to draw a sample of blood by puncturing a vein or invading a capillary. Then, using a widely accepted technique, the sample of blood is subjected to a high speed centrifuge treatment for several minutes (e.g., 7 or more minutes). The centrifuging process, if properly carried out, separates the corpuscles into a packed mass. The volume occupied by the packed corpuscles, expressed as a percentage of the total volume of the plasma/corpuscle combination, is taken as the hematocrit.

It will be appreciated that the centrifuge process provides a hematocrit value which includes all corpuscles, not just red corpuscles. Nevertheless, the vastly greater numbers of red corpuscles in a healthy subject allows the hematocrit value obtained by the centrifuge process to be clinically, usable in such healthy subjects. Nevertheless, in subjects with low hematocrit or dramatically high white corpuscle content, it may be desirable to diminish the effect of the non-red corpuscles when obtaining an hematocrit value.

There have been various techniques and devices introduced which have automated and increased the precision of obtaining a hematocrit value. Nevertheless, all the previously available techniques have one or more drawbacks.

Specifically, the previously available techniques all require that a sample of blood be withdrawn from the patient for in vitro analysis. Any invasion of the subject to obtain blood is accompanied by the problems of inconvenience, stress, and discomfort imposed upon the subject and also the risks which are always present when the body is invaded. Drawing blood also creates certain contamination risks to the paramedical professional. Moreover, even in a setting where obtaining a blood sample does not impose any additional problems, e.g., during surgery, the previously available techniques require a delay between the time that the sample is drawn and the hematocrit value is obtained. Still further, none of the previously available techniques allow continuous monitoring of a subject's hematocrit, as might be desirable during some surgical procedures or intensive care treatment, but require the periodic withdrawal and processing of blood samples.

In view of the drawbacks inherent in the available art dealing with invasive hematocrit determinations, it would be an advance in the art to noninvasively and quantitatively determine a subject's hematocrit value. It would also be an advance in the art to provide a system and method for noninvasive hematocrit monitoring which can be applied to a plurality of body parts and which utilizes electromagnetic emissions as an hematocrit information carrier. It would be another advance in the art to provide a system and method which can provide both immediate and continuous hematocrit information for a subject. It would be yet another advance to provide repeatable and reliable systems for noninvasive monitoring of a subject's hematocrit. It would be still another advance in the art to noninvasively and accurately determine a subject's blood oxygen saturation while accounting for the patient's low or varying hematocrit and/or under conditions of low perfusion.

BRIEF SUMMARY AND OBJECTS OF THE INVENTION

The present invention is directed to apparatus and methods for determining biologic constituent values, such as the hematocrit value, transcutaneously and noninvasively. This is achieved by passing at least two wavelengths of light onto or through body tissues such as the finger, earlobe, or scalp, etc. and then compensating for the effects body tissue and fluid effects. As used herein, the term biologic constituent includes proteins, red cells, metabolites, drugs, cytochromes, hormones, etc.

In one embodiment within the scope of the present invention, the wavelengths of light are selected to be near or at the isobestic points of reduced hemoglobin and oxyhemoglobin to eliminate the effects of variable blood oxygenation. At an isobestic wavelength, the extinction coefficient, $\epsilon$, is the same for both reduced and oxygenated hemoglobin. Thus, at isobestic wavelengths, the amount of light absorption is independent of the amount of oxygenated or reduced hemoglobin in the red cells.

Means are provided for delivering and detecting those wavelengths of light and for analyzing the light intensities. The sensing and radiation emitting elements are preferably spatially arranged to allow ease of use and to be accessible to a patient's exterior body parts. The configuration of the sensing and emitting elements is important to give optimum repeatability of the signals and data derived therefrom.

Memory and calculation means are included which are capable of storing, manipulating, and displaying the detected signals in a variety of ways. For instance, the continuous pulse wave contour, the pulse rate value, the hematocrit value and the continuous analog hematocrit curve in real time, the hematocrit-independent oxygen saturation value, and the oxygen content value of the blood, all as digital values or as continuous analog curves in real time are capable of being displayed.

An important advantage of monitoring and analyzing each individual pulsatile signal is that averaging algorithms may be performed for identifying and rejecting erroneous data. In addition, such techniques also improve repeatability.

Another significant advantage of the present invention is the capability of monitoring multiple wavelengths (including nonisobestic wavelengths) for the simultaneous real time computation and display of the hematocrit-independent oxygen saturation value. Techniques in prior art oximetry have all suffered inaccuracies due to hematocrit sensitivities.

Rather than apply AC-DC cancellation techniques only, it is also within the scope of the present invention to detect and analyze multiple wavelengths using a logarithmic DC analysis technique. In this embodiment, a pulse wave is not required. Hence, this embodiment may be utilized in states of low blood pressure or low blood flow.

It is, therefore, a primary object of the present invention to provide a system and method for noninvasively and quantitatively determining a subject's hematocrit or other blood constituent value.

It is another object of the present invention to noninvasively determine the hematocrit of a subject by utilizing electromagnetic radiation as the transcutaneous information carrier.

It is another object of the present invention to provide a noninvasive hematocrit monitor which may be used on various body parts and which provides accurate quantitative hematocrit values.

It is another object of the present invention to provide a system and method which can provide immediate and continuous hematocrit information for a subject.

It is yet another object of the present invention to provide a repeatable and reliable system for noninvasive monitoring of a subject's hematocrit.

It is still another object of the present invention to provide a system and method for noninvasively determining a subjects's blood oxygen saturation ($S_aO_2$) independent of the subject's hematocrit.

It is still another object of the present invention to provide a system and method for noninvasively determining a subject's hematocrit and/or blood oxygen saturation even under conditions of low perfusion (low blood flow).

These and other objects and advantages of the invention will become more fully apparent from the description and claims which follows, or may be learned by the practice of the invention.

BRIEF DESCRIPTION OF THE DRAWINGS

FIG. 1B is an enlarged cross sectional view of the body part (finger) and associated system components represented in FIG. 1 used in a reflective mode.

FIG. 2 is a chart showing the optical absorption coefficients of oxyhemoglobin ($HbO_2$), reduced hemoglobin (Hb), and water ($H_2O$) versus wavelength.

FIGS. 7A–7C provide a detailed schematic diagram digital section circuitry included in the presently preferred system of the present invention.

FIGS. 8A–8D provide a detailed schematic diagram of the analog section circuitry included in the presently preferred system of the present invention.

FIG. 11 is a graph of $\epsilon_{b805}/\epsilon_{b970}$ versus Hematocrit.

DETAILED DESCRIPTION OF THE PREFERRED EMBODIMENTS

Figure 1:
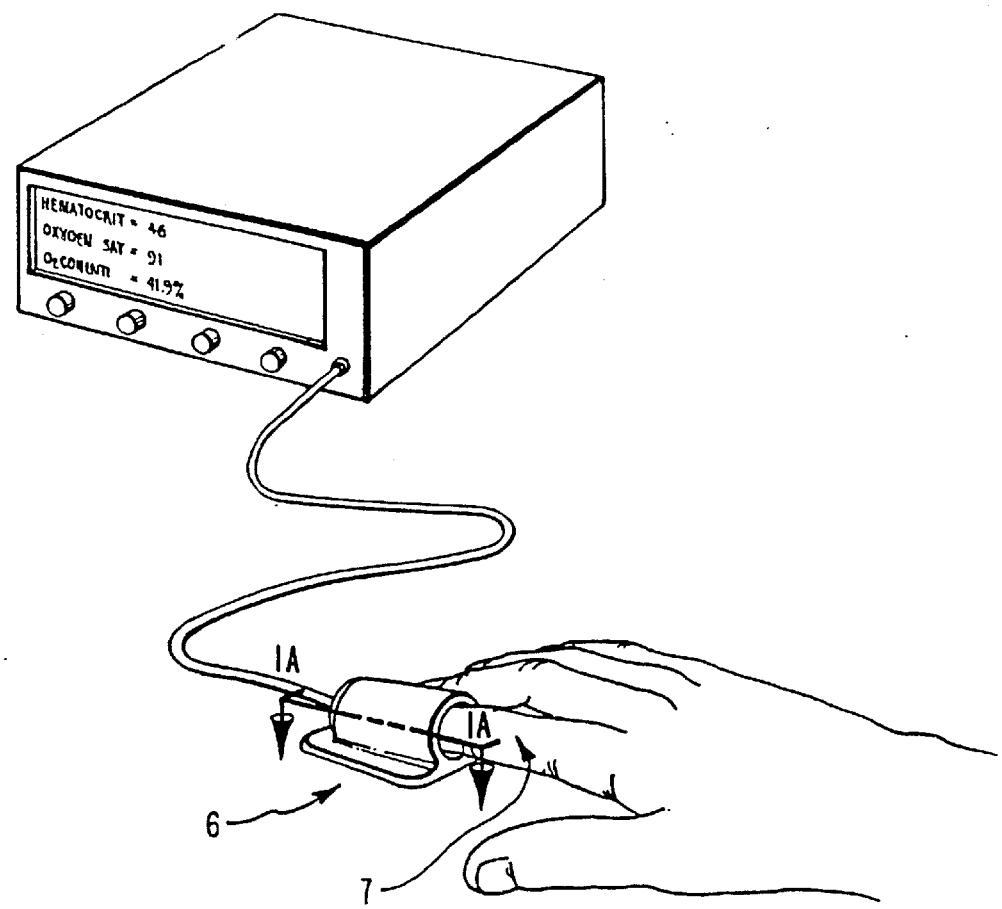
FIG. 1 is a perspective, view of a first presently preferred embodiment of the present invention.

The present invention is directed to apparatus and methods for determining biologic constituent values, such as the hematocrit value, transcutaneously and noninvasively. This is achieved by passing at least two wavelengths of light onto or through body tissues such as the finger, earlobe, or scalp, etc., and then compensating for the effects of body tissue and fluid by modifying the Beer-Lambert Law. The principles within the scope of the present invention may also be utilized to provide a hematocrit-independent oxygen saturation and oxygen content measurements as well as noninvasive measurement of blood constituents such as glucose, cholesterol, bilirubin, creatinine, etc.

Although the present invention will describe in great detail the transillumination of various body parts, it will be appreciated that reflectance spectrophotometry may alternatively be employed where transillumination is difficult to accomplish. As used herein, the term "body part" is intended to include skin, earlobe, finger, lip, forehead, etc. Because the principles within the scope of the present invention can be adapted by those skilled in the art for in vitro measurement of hematocrit and other blood constituents, the discussion relating to body parts is intended to apply to various in vitro blood containers such as tubes and cuvettes.

1. Spectrophotometric Methods

Spectrophotometric methods have been described in the prior art which monitor various metabolites in body fluids. Radiation, typically in the visible or near infrared region, is directed onto an exterior body part for transcutaneous penetration of the radiation. The radiation is then monitored reflectively or transmissively by a photodetector or similar sensor. Radiation spectra are chosen at wavelengths where the metabolite or compound sought for either absorbs highly or poorly. Some examples of such spectrophotometric methods are described in U.S. Pat. No. 4,653,498 for pulse oximetry, U.S. Pat. No. 4,655,225 for blood glucose monitoring, and more recently U.S. Pat. No. 4,805,623 for monitoring various blood metabolites (glucose, cholesterol, etc.).

A theoretical basis for the spectrophotometric techniques is the Beer-Lambert Law:

$$I = I_0 e^{-\epsilon X d} \tag{1}$$

Equation (1) may also be written:

$$\ln(I/I_0) = -\epsilon X d \tag{1a}$$

wherein $I_0$ is the incident intensity of the source radiation, I is the transmitted intensity of the source through the sample, $\epsilon$ is the extinction coefficient of the sought for component, X is the concentration of the sample component in the tissue itself, and d is the optical path length (distance).

The Beer-Lambert Law (1) permits in vitro solute concentration determinations. However, quantitative measurements have not been possible in the body since the scattering of the incident photons passing into and through the integument and subdermal regions is extensive and highly variable. This scattering spoils the Beer-Lambert Law by adding a variable loss of radiation to the measurement and also extends the path length of the incident photons by an unknown amount as well.

Even though optical pulse rate monitors, plethysmographs, and pulse oximeters are known, their development has been accelerated by techniques which allow for cancellation of the optical scattering effects to a large extent. This development began with U.S. Pat. No. 2,706,927 and was further refined by Yoshiya, et. al. (Med. and Biol. Eng. and Computing, 1980 Vol. 18, Pages. 27–32), Koneshi in U.S. Pat. No. 3,998,550, and Hamaguri in U.S. Pat. No. 4,266,554, which utilized a technique of analyzing the resultant opto-electronic signal by dividing it into its AC and DC components. The AC and DC components are manipulated with logarithmic amplifiers in such a way as to eliminate the above-mentioned transdermal optical effects (the variable amount of radiation loss due to scattering in the tissue and the unknown and variable amounts of optical path length increase).

Until now, the AC-DC cancellation techniques have not been successfully adapted for the measurement of hematocrit or hematocrit-independent blood oxygen saturation.

2. Noninvasive Differential-ratiometric Spectrophotometry

It is assumed that incident radiation passing onto or into a living tissue will pass through a combination of blood, tissue, and interstitial fluid compartments. The light attenuated by such a living tissue can be expressed by the modified Beer-Lambert equation:

$$\text{ti } I = I_0 e^{-(\epsilon_b(X_a + X_v) + \epsilon_t X_t + \epsilon_i X_i)d + G} + \text{tm} \tag{2}$$

Equation (2) may also be written $$\ln(I/I_0) = -(\epsilon_b(X_a + X_v) + \epsilon_t X_t + \epsilon_i X_i)d + G \tag{2a}$$

Where $\epsilon_b$, $\epsilon_t$, and $\epsilon_i$ represent the extinction coefficient in the blood, tissue, and interstitial fluid compartments, respectively; $X_a$ and $X_v$ represent the arterial and venous blood, concentration ($X_b = X_a + X_v$), $X_t$ represents the concentration of the tissue absorbers, and $X_i$ represents the relative concentration of water and dissolved components in the interstitial fluid compartment; d represents the intrasensor spacing; and G is a constant of the geometric configuration.

As the blood layer pulsates, the concentration terms change. The term d can be fixed by the geometric configuration of the device. Taking the partial derivatives of equation (2) with respect to time and dividing by equation (2) gives:

$$-\frac{\partial I/\partial t}{I} = (\epsilon_b(\partial X_a/\partial t + \partial X_v/\partial t) + \epsilon_t \partial X_t/\partial t + \epsilon_i \partial X_i/\partial t)d + \partial G/\partial t \tag{3}$$

which can be simplified at each compartment and wavelength by letting $X' = \partial X/\partial t$, and $G' = \partial G/\partial t$, and $$V'_\lambda = -\left(\frac{\partial I/\partial t}{I}\right)_\lambda$$

to give $$V'_\lambda = (\epsilon_b(X'_a + X'_v) + \epsilon_t X'_t + \epsilon_i X'_i)d + G' \tag{4}$$

Assuming that $X_t$ and G do not vary significantly over the pulse time interval, then $G'=0$ and $X'_t=0$, and equation (4) can be simplified to $$V'_\lambda = (\epsilon_b(X'_a + X'_v) + \epsilon_i X'_i)d \tag{5}$$

Examining the transport between $X_a$ and $X_v$, we can form a proportionality constant $K_v$ such that $X'_v = K_v X'_a$, representing the reactionary nature of the venous component, and further reduce the above equation to $$V'_\lambda = (\epsilon_b(1-K_v)X'_a + \epsilon_i X'_i)d \tag{6}$$

Since $X'_a$ and $X'_i$ are not wavelength ($\lambda$) dependent, $V'_\lambda$ values at different wavelengths can be differentially subtracted to produce a hematocrit independent term which contains only $\epsilon_i X'_i$ information. Although the term $V'_{805}/V'_{1310}$ provides useful information regarding relative changes in hematocrit, it should be recognized that the simple $V'_{805}/V'_{1310}$ ratio is not sufficiently accurate for hematocrit value determination unless the $\epsilon_i X'_i$ term is known or eliminated. For example, the $\epsilon_i X'_{i805}$ term can be neglected since $\epsilon_{i805}$ is extremely small, whereas the $\epsilon_i X'_{i1310}$ term is about 25%–50% of the $\epsilon_{b1310}$ value of blood itself and cannot, therefore, be neglected without affecting accuracy.

Figure 16:
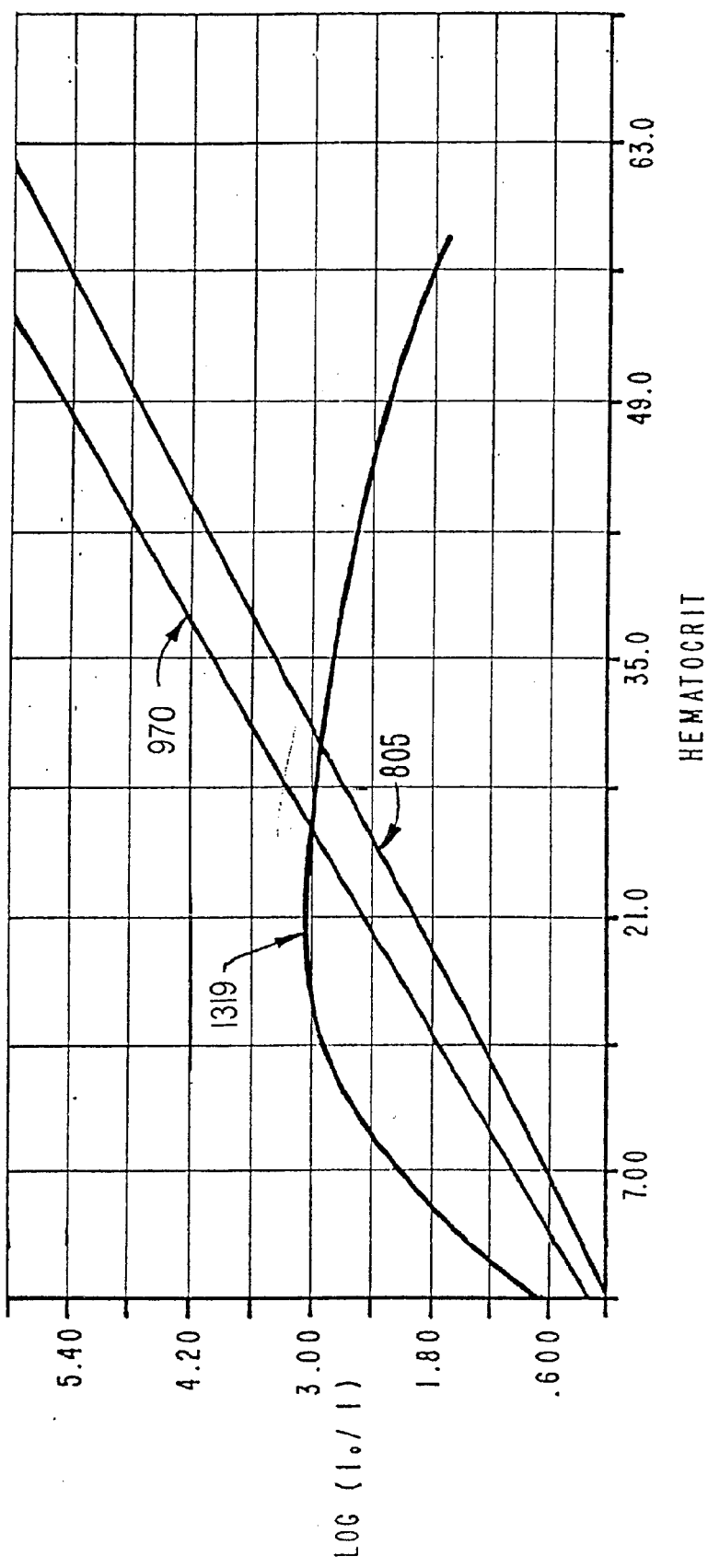
FIG. 16 is a chart showing the relationship between the extinction coefficient of light at three different wavelengths versus hematocrit for whole blood.

FIGS. 11 and 16 suggest that a linear combination of $V'_\lambda$ at $\lambda = 805$ nm and $\lambda = 970$ nm will have a near constant value for a range of Hct values. Since the extinction coefficients $\epsilon_{i805}$ and $\epsilon_{i970}$ are well known, or can be empirically determined, a precise proportionality constant $R_1.1$ can be found to produce $$\epsilon_{i970}X_i' = V_{970}' - R_1 V_{805}' \qquad (7)$$

This correction term can now be applied with a second proportionality constant $R_2$ (where $R_2$ is approximately equal to $\epsilon_{i1310}/\epsilon_{i970}$) to the $V'_{1310}$ term to exactly remove its $\epsilon_{i1310}X'_i$ sensitivity, hence:

$$\epsilon_{b1310}(1-K_v)X_a' = V_{1310}' - R_2(V_{970}' - R_a V_{805}') \qquad (8)$$

Figure 3:
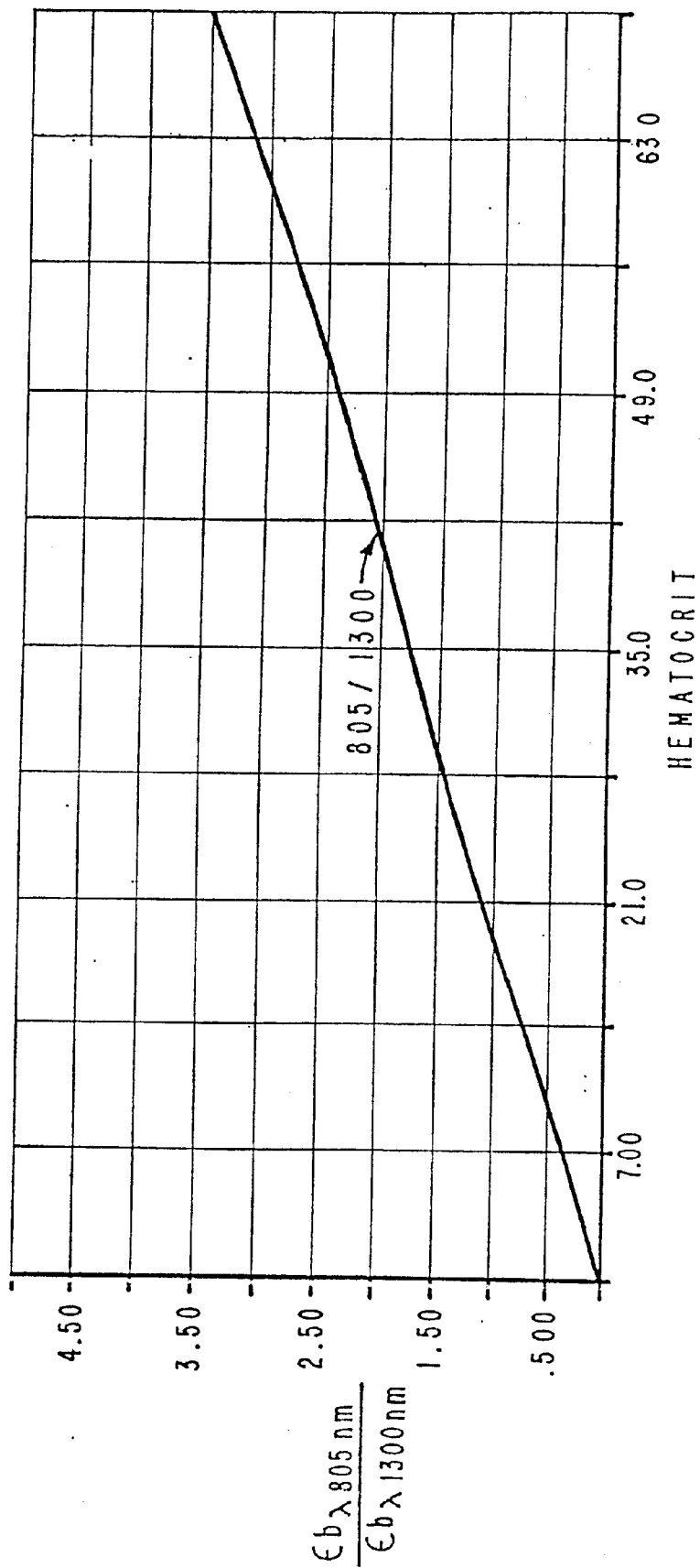
FIG. 3 is a chart showing the relationship between the ratio of the extinction coefficients of two rays having differing wavelengths versus hematocrit.
Figure 4A:
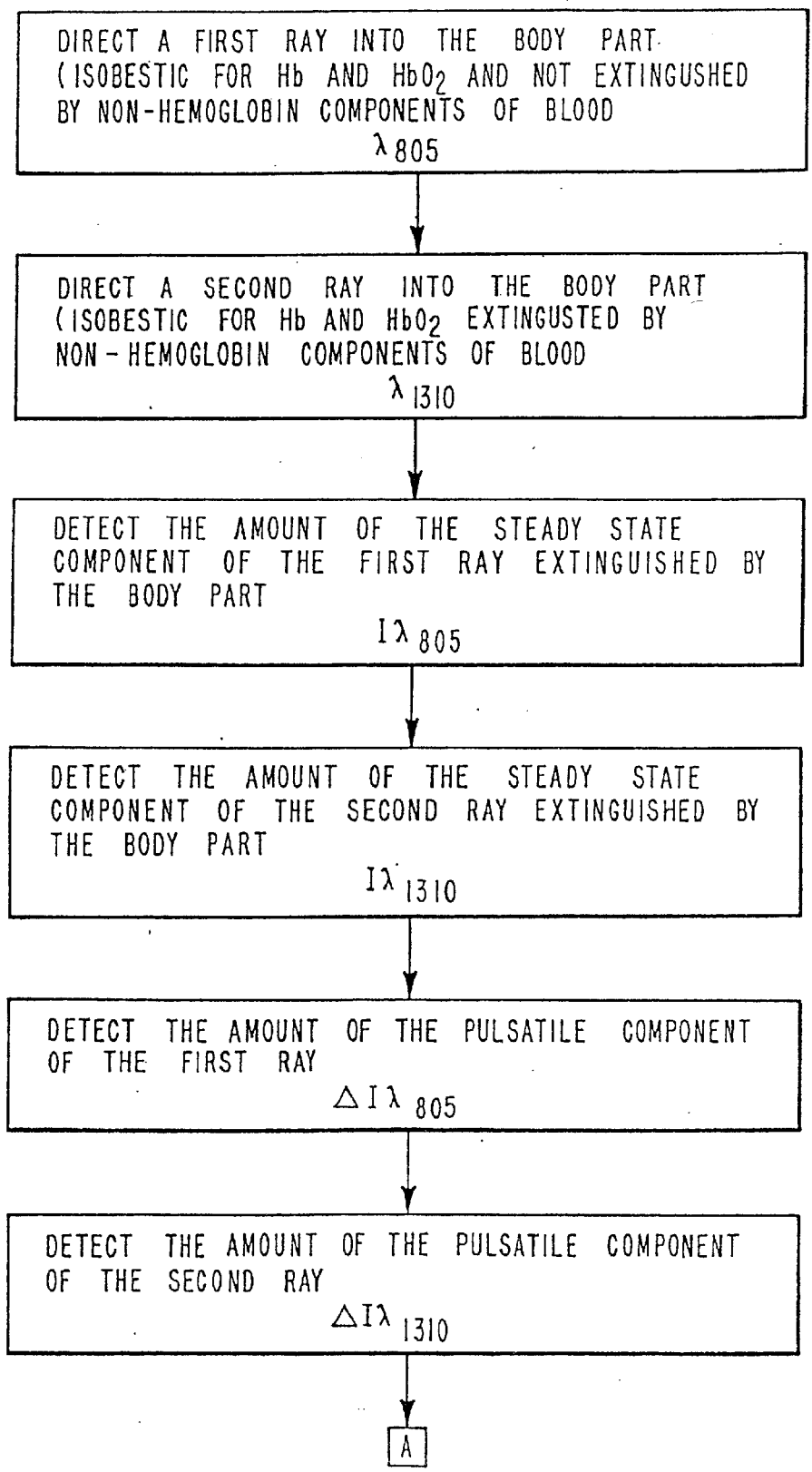
FIGS. 4A–4D provide a flow chart showing the steps carried out during one presently preferred method of the present invention using a pulsatile component of the subject's blood flow to provide accurate hematocrit and blood oxygen saturation values.
Figure 4B:
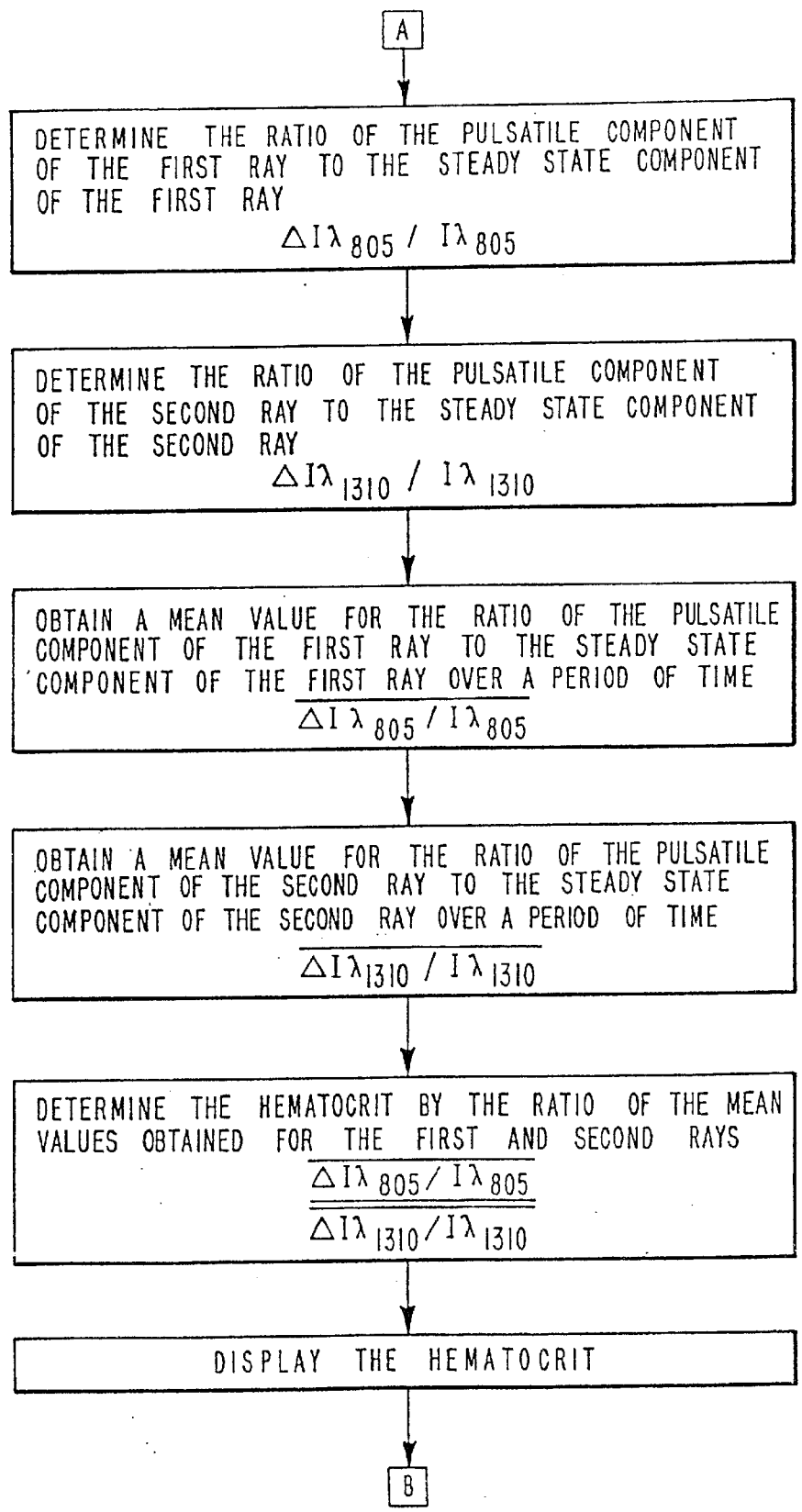
Figure 4C:
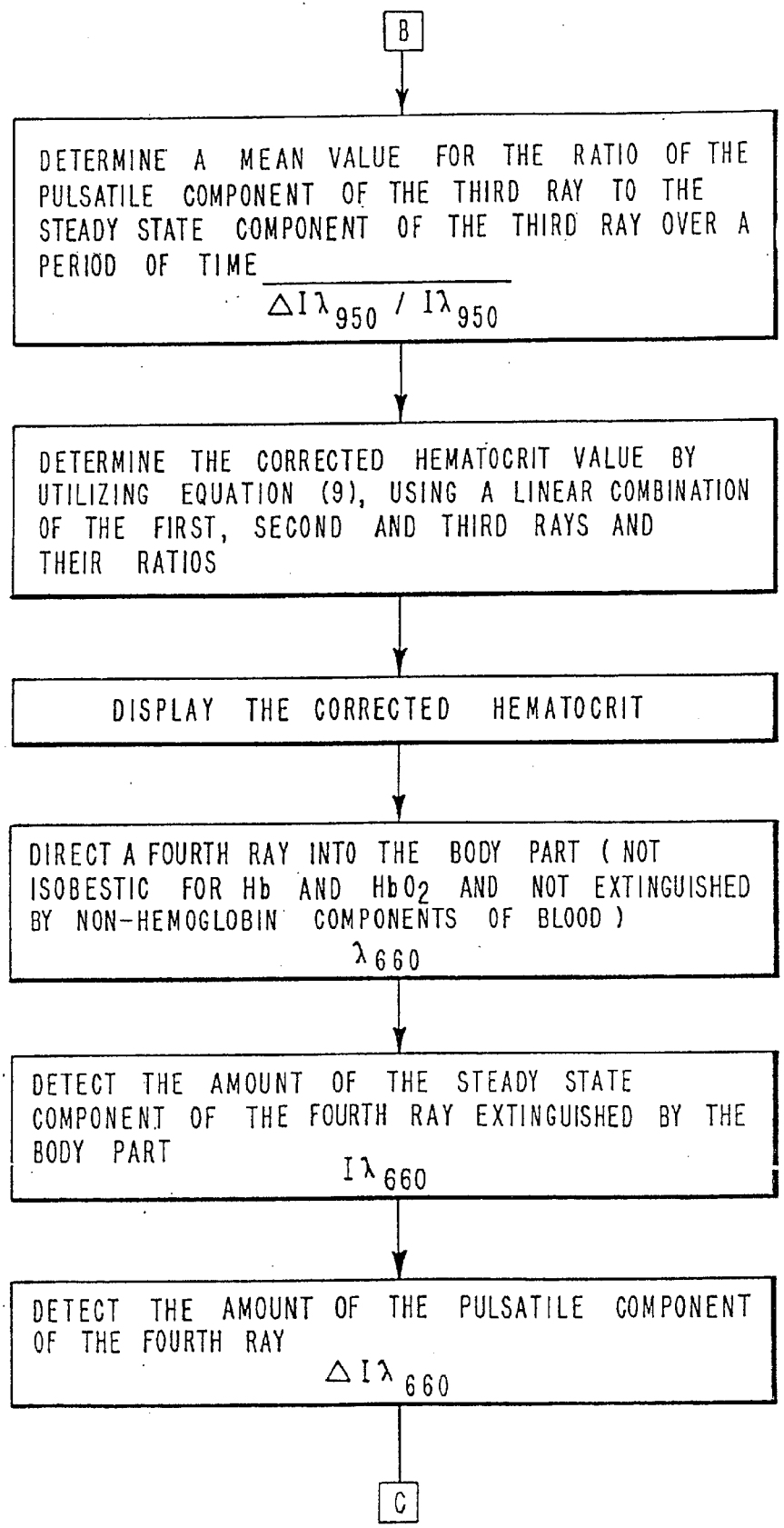
Figure 4D:
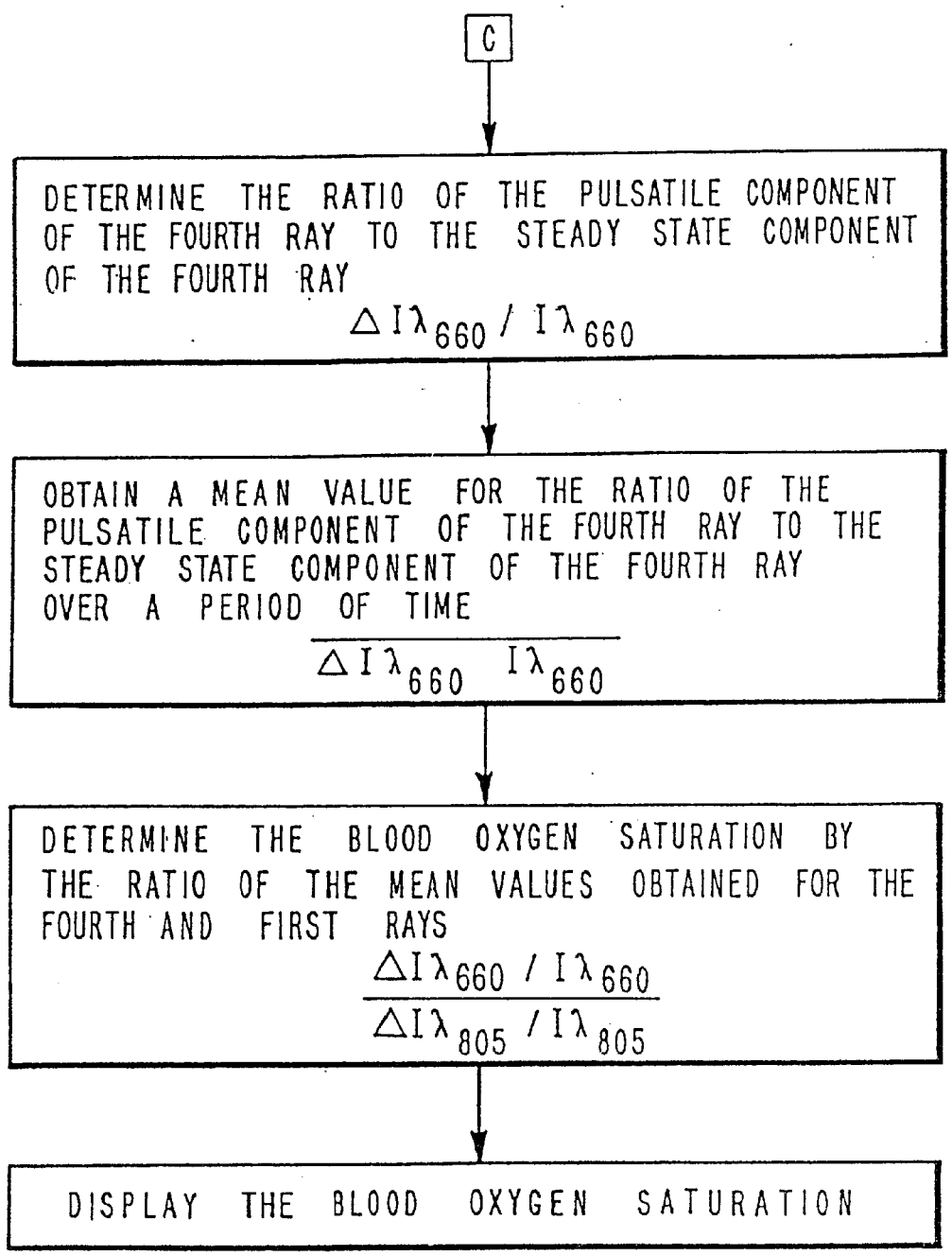
Figure 5:
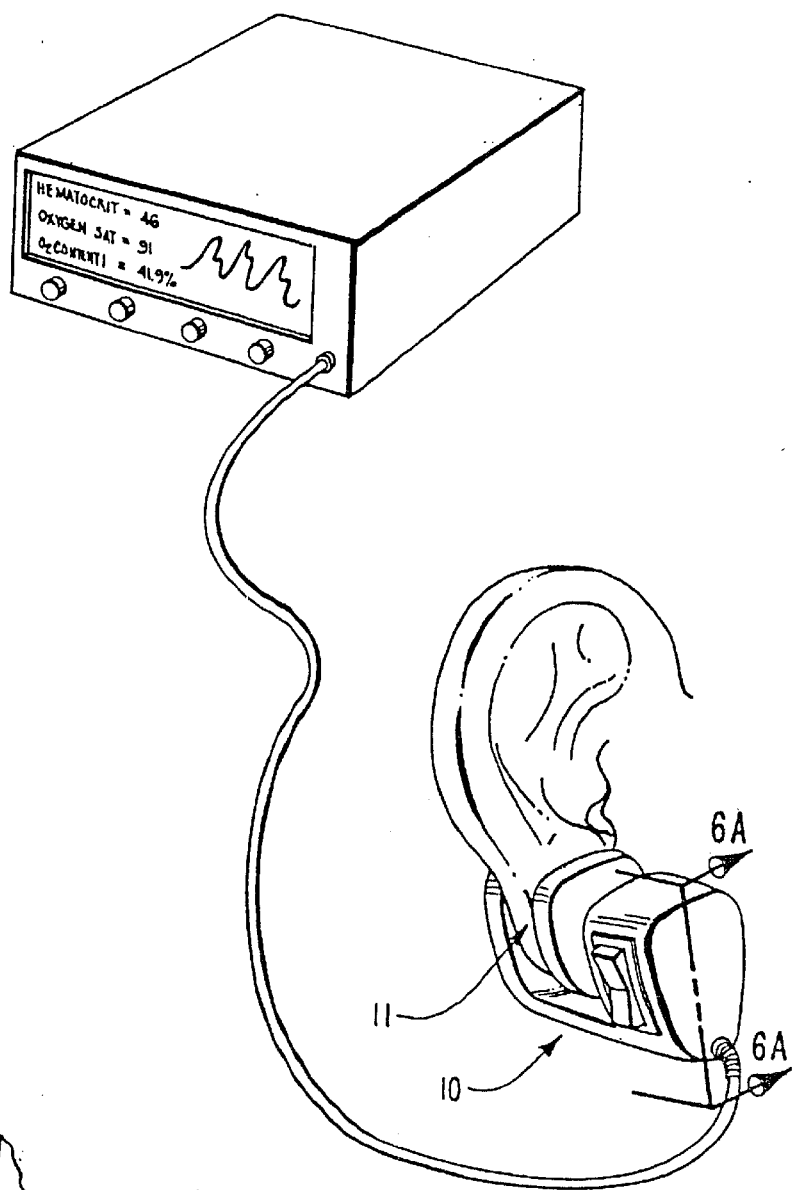
FIG. 5 is a perspective view of a second presently preferred system of the present invention which is applied to the ear and includes structures to squeeze out the blood to blanch the ear tissues.
Figure 5A:
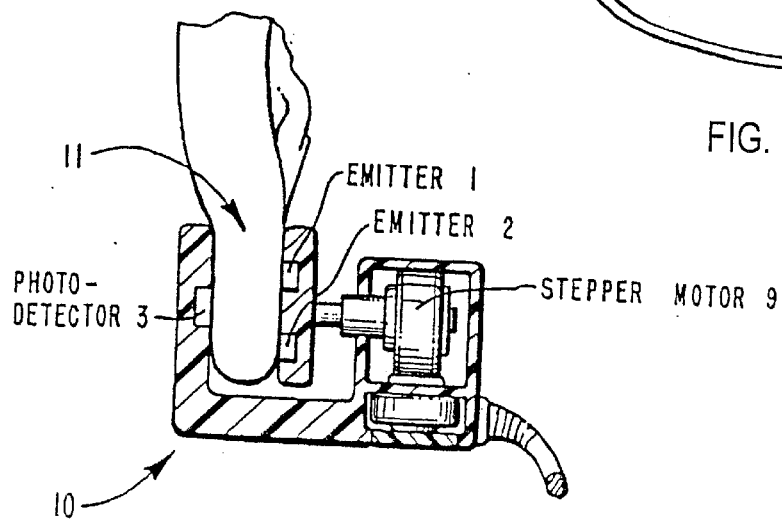
FIG. 5A is an enlarged cross sectional view of the ear and system components

This corrected term can now be used ratiometrically with $V_{805}'$ to remove the $(1-K_v)X'_a$ and leave the pure extinction coefficient ratio represented by Equation (9) below and shown graphically in FIG. 3.

$$\frac{\epsilon_{b805}}{\epsilon_{b1310}} = \frac{V'_{805}}{V'_{1310} - R_2(V'_{970} - R_1 V'_{805})} \qquad (9)$$

It should be noticed that the following assumptions and requirements are essential in hematocrit determinations (but in the case of pulse oximetry these requirements may not be of the same degree of significance).

A. Even though wavelengths λ=805 nm and λ=1310 nm are near isobestic, the actual function of ε versus Hematocrit at each given wavelength must hold hematocrit information that is different in curvature, or offset, or linearity, or sign from the other. See FIG. 16. If the functions $\epsilon_\lambda$ versus hematocrit are not sufficiently different, then the ratio $\epsilon_{b\lambda 1}/\epsilon_{b\lambda 2}$ will not hold hematocrit information. See FIGS. 12A and 12B and FIGS. 13A and 13B. Even though the foregoing discussion refers to the isobestic wavelengths of λ=805 nm and λ=1310 nm, it will be appreciated that other isobestic wavelengths, such as λ=570 nm, λ=589 nm, and λ=1550 nm, may also be utilized.

B. Further, the wavelengths should be selected close enough to one another such that the optical path lengths, d, are approximately the same. Longer wavelengths are preferred since they exhibit less sensitivity to scattering, s:

$$s \propto \frac{1}{\lambda^2} \qquad (10)$$

Figure 14:
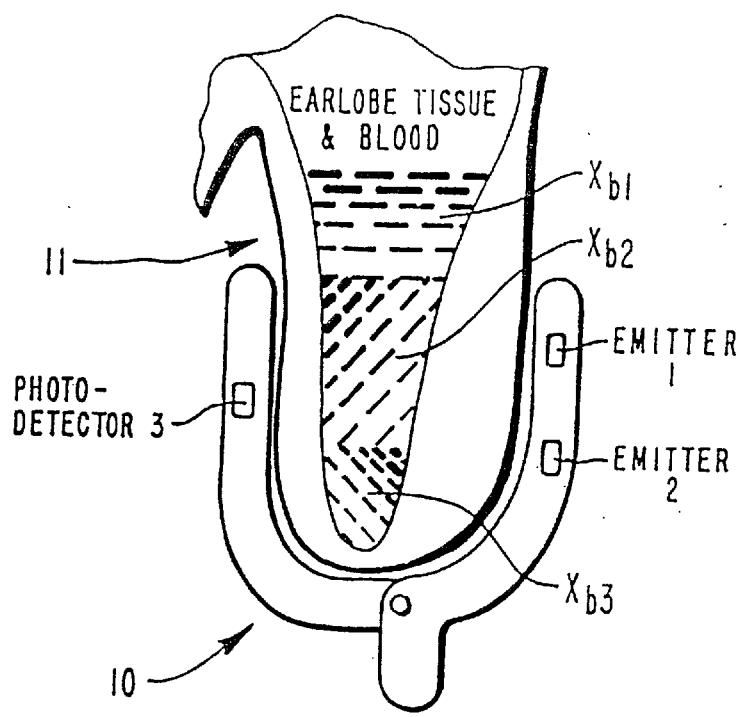
FIG. 14 illustrates vertical sensor-emitter alignment and the resulting non-identical $\Delta X_b$ regions.
Figure 15:
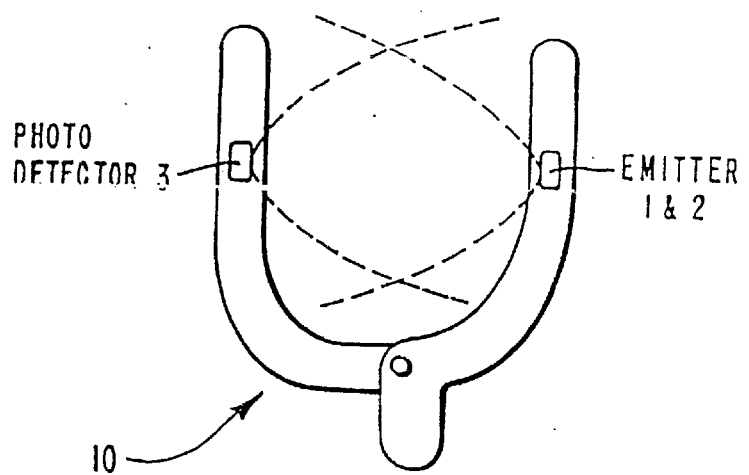
FIG. 15 illustrates horizontal sensor emitter alignment.

C. The geometric or spatial relationship of the emitters and sensors is important. For instance, if vertically aligned emitters are used in an earlobe-measuring device, then the top-most emitter may illuminate a different amount of blood filled tissue than the lower emitter. If only one sensor is used, then there will be a disparity between $X'_b$ at each wavelength. See FIG. 14, wherein $X_{b1} > X_{b2} > X_{b3}$. Furthermore, the sensor-emitter spatial separation distance is very important because the pressure applied to the tissue between the sensor and emitters affects the arteriolar and capillary vessel compliance. This changes the X' as the pressure (or distance) changes. This change in X' then modulates the $V'_\lambda$ function. Therefore, the sensor-emitter separation distance must be such that the pressure applied to the earlobe, fingertip, or other body member, does not affect the $V'_\lambda$ function. This sensor separation distance is empirically determined and should generate less than 40 mm Hg applied transmural pressure.

A horizontal alignment (FIG. 14) of the emitters with respect to the single sensor can be arranged so that the emitters and sensors illuminate and detect identical regions of $\partial X_{\lambda 1}$ and $\partial X_{\lambda 2}$. It is important to note that the term d, the sensor-emitter separation, will be different between $\lambda_1$ and $\lambda_2$ by the cosine of the angle between the sensor and emitter. Therefore, if any misalignment from normal occurs, the term d will not cancel to obtain equation (9).

The preferred arrangement is wherein all the emitters (660, 805, 950, and 1310 nm) are located on the same substrate. This is preferred because the emitters will then illuminate essentially the same $X_b$ region.

D. In the case of reflectance spectrophotometry, an aperture for the sensor and each emitter is required. See FIG. 1B. Also, a sensor-emitter separation is required so that the reflectance of the first layer of tissue, $R_t$, (a non-blood layer of epithelium) does not further exaggerate a multiple scattering effect, i.e. the total reflectance, R, measured would contain spurious information of the epithelial layers' reflectance as well, where:

$$R = R_t + \frac{T_t^2 \cdot R_b}{(1 - R_b \cdot R_t)} \qquad (11)$$

where R is the total reflectance, $R_t$ is the reflectance due to the first tissue-epithelial layer, $R_b$ is the reflectance due to the blood layer, and $T_t$ is the transmission through the first tissue layer.

The reflectance equations describing $R_t$ or $R_b$ must now sum all of the backscattered light that the sensor detects, i.e.,:

$$R_b = \iiint (\text{source function}) \cdot (\text{scattering function}) \qquad (12)$$

While equation (9) describes the theory of the noninvasive hematocrit device, the four assumptions (A–D) are important to the repeatability and accurate functioning of the hematocrit device.

Assuming items A through D are dealt with appropriately, then (9) becomes:

$$\frac{\epsilon_{b\lambda 1}}{\epsilon_{b\lambda 2}} = \frac{(s_1 + k_1)}{(s_2 + k_2)} \qquad (13)$$

where s is a scattering constant and k is an absorption constant, and where in whole blood:

$$s = \sigma_s Hct(1-Hct) \qquad (14)$$

$$k = \sigma_a Hct(\text{at isobestic wavelengths}) \qquad (15)$$

where $\sigma_s$ is the scattering cross section and $\sigma_a$ is the absorption cross section.

From the foregoing, e, the extinction coefficient, is not a simple function of the absorption coefficient, k, normally determined in pure solutions. Rather, it contains a diffusion or scattering term, s, which must be accounted for in a non-pure solution media such as whole blood and tissue.

Finally, substituting (14) and (15) into (13):

$$\frac{\epsilon_{\lambda 1}}{\epsilon_{\lambda 2}} = \frac{\sigma_{s1}(1 - Hct) + \sigma_{a1}}{\sigma_{s2}(1 - Hct) + \sigma_{a2}} \qquad (16)$$

Therefore, the ratio $\epsilon_{\lambda 1}/\epsilon_{\lambda 2}$ is a function of hematocrit. From FIG. 3, a look up table or polynomial curve fit equation may be obtained and utilized in the final displayed hematocrit results. Knowing the actual hematocrit value, it is straightforward to see (FIG. 2) that a wavelength at 660 nanometers can be selected to obtain an ε ratio wherein the hematocrit-independent oxygen saturation value is derived. For example, equation (16) would become:

$$\frac{\varepsilon_{b660}}{\varepsilon_{b805}} = \frac{\sigma_{s660}(1-Hct) + \sigma_{a660} - S_aO_2(\sigma_{ao660} - \sigma_{ar660})}{\sigma_{s805}(1-Hct) + \sigma_{a805} - S_aO_2(\sigma_{ao805} - \sigma_{as805})} \quad (17)$$

Equation (17) shows both the hematocrit and oxygen saturation dependence on each other.

Figure 10:
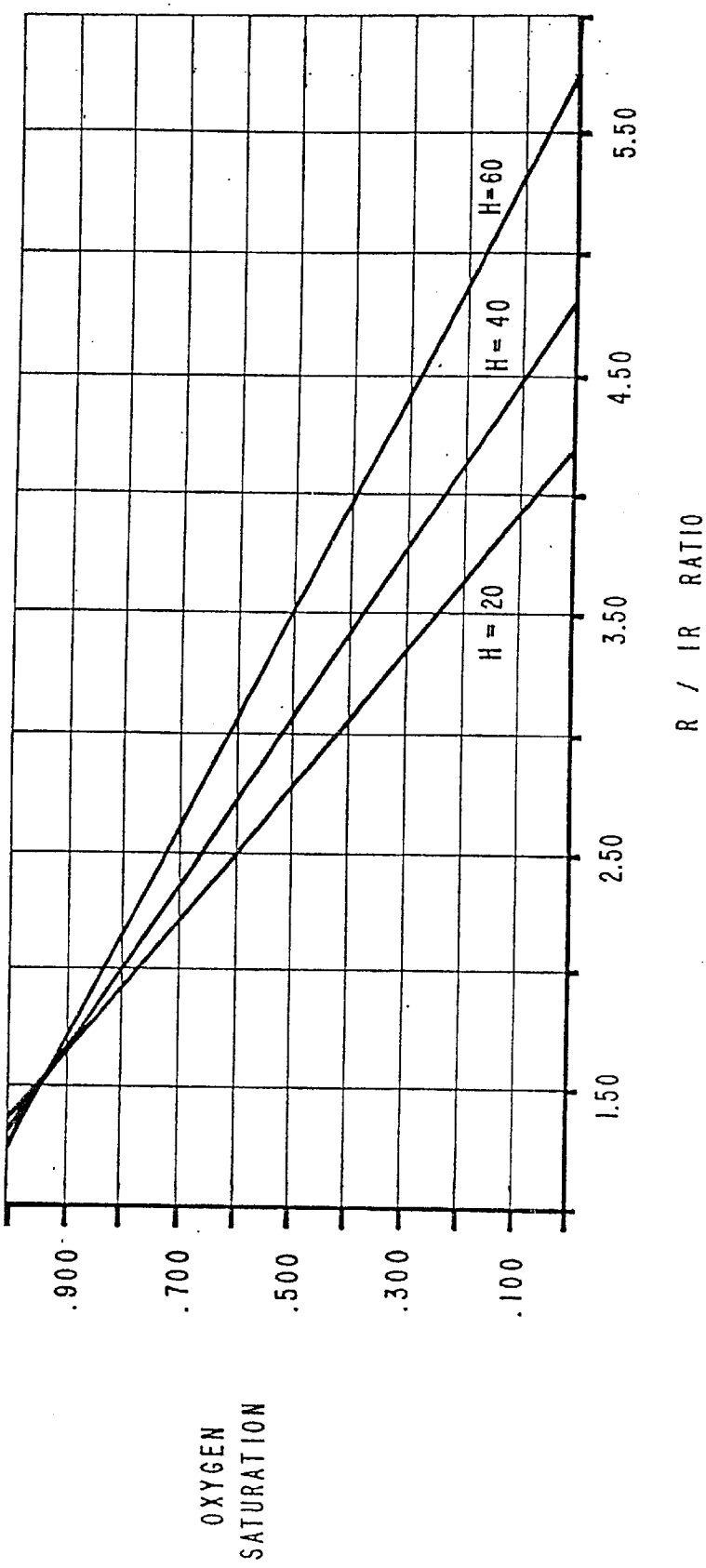
FIG. 10 is a graph showing variation in oxygen saturation as a function of hematocrit.
Figure 12A:
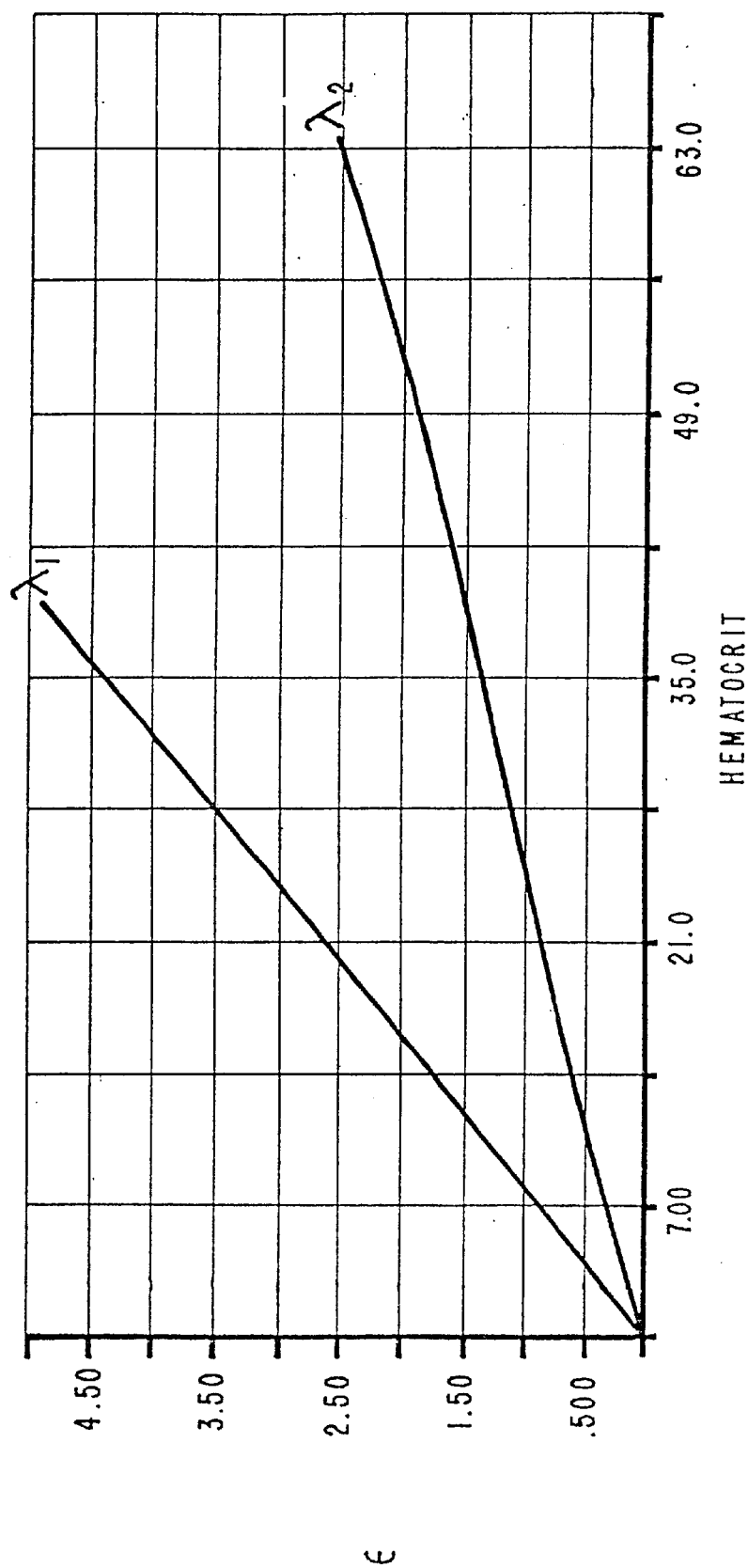
FIGS. 12A–12B are graphs of $\epsilon$ versus Hematocrit at two non-preferred wavelengths and $\epsilon_1/\epsilon_2$ versus Hematocrit at those non-preferred wavelengths.
Figure 12B:
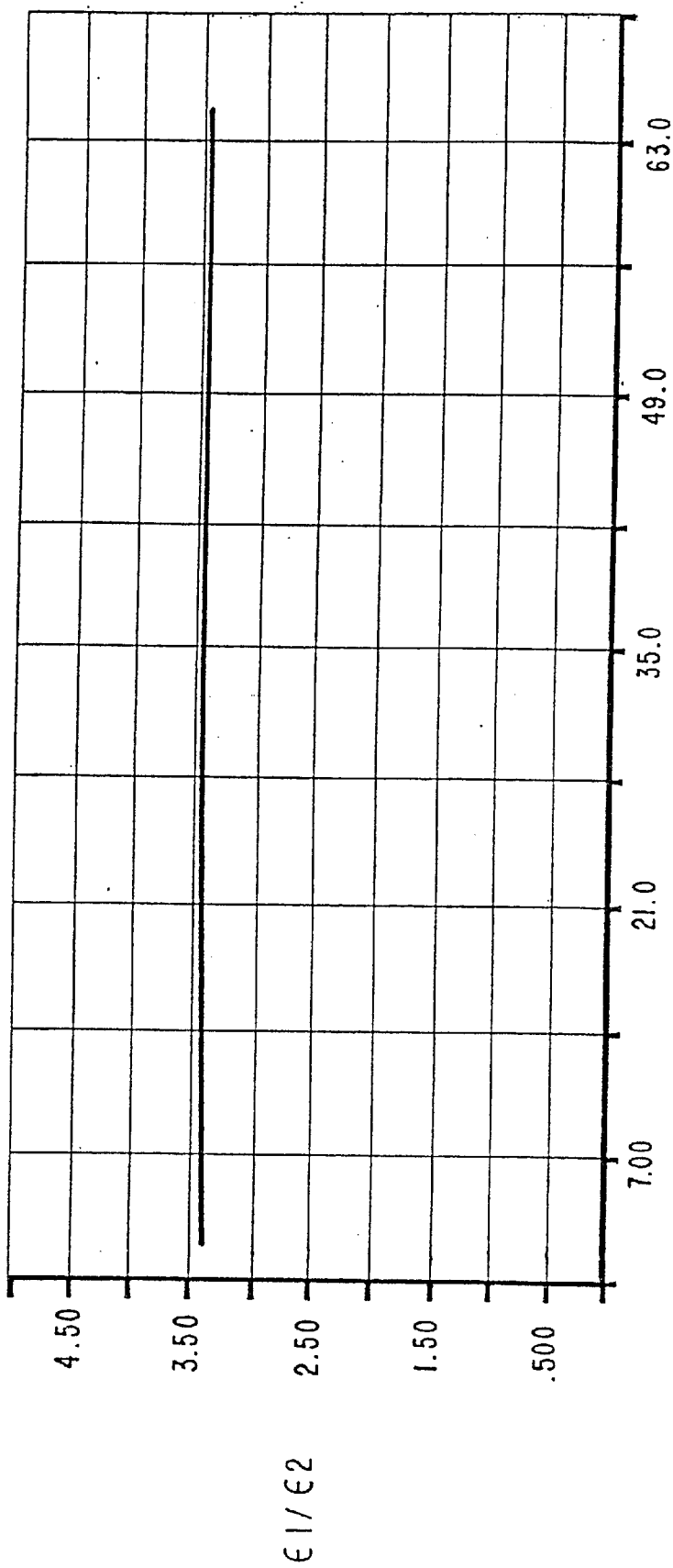
Figure 13A:
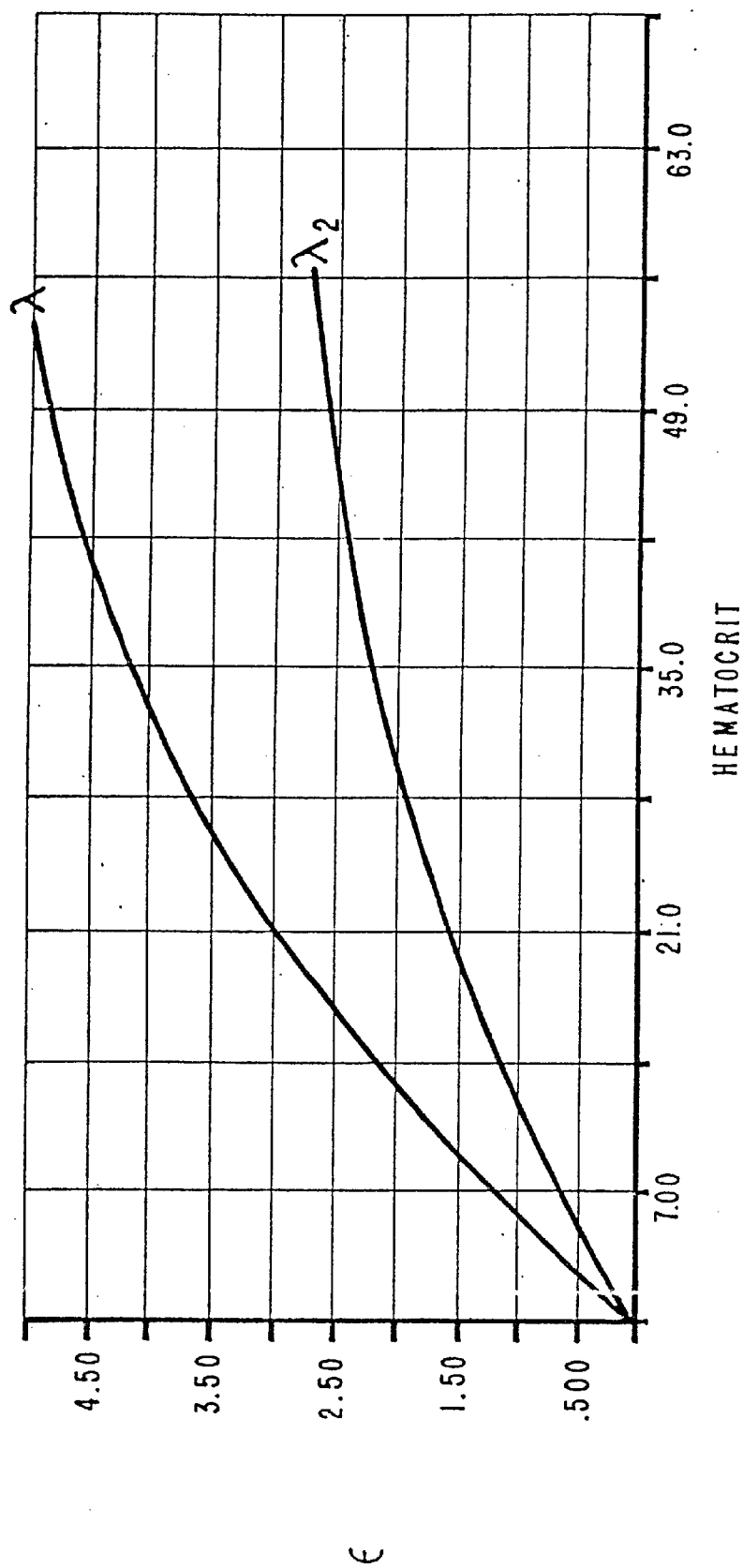
FIGS. 13A–13B are graphs of $\epsilon$ versus Heniatocrit at two non-preferred wavelengths and $\epsilon_1/\epsilon_2$ versus Hematocrit at those non-preferred wavelengths.
Figure 13B:
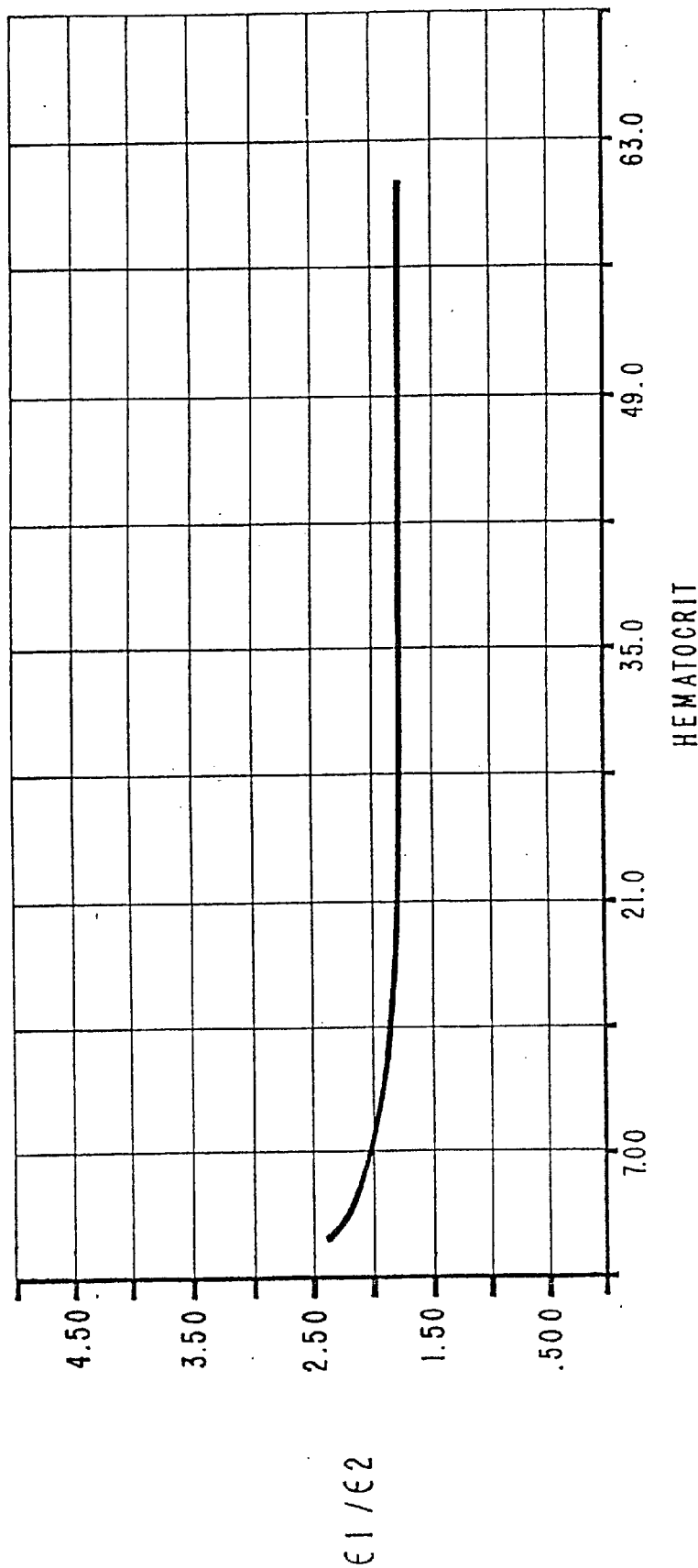

FIG. 10 graphically demonstrates the need for a hematocrit-independent blood saturation device. As either the hematocrit value or percent oxygen saturation decreases, the percent saturation error becomes unacceptable for clinical usage. For example, it is not uncommon to see patients with a low hematocrit (about 20%) who have respiratory embarrassment (low oxygen saturation) as well. Hence, the clinician simply requires more accurate oxygen saturation values.

Knowing the hematocrit and oxygen saturation values, the computation of the Oxygen Content is trivial and may be displayed directly (a value heretofore unavailable to the clinician as a continuous, real-time, noninvasive result):

$$[\text{Oxygen Content}] = Hct \cdot S_aO_2 \cdot K \quad (18)$$

where K is an empirically determined constant.

Referring to the equations (16) and (9) a decision must be made by the computer as to the suitability of utilizing the Taylor expansion approximation to the logarithm. This algorithm is maintained in the software as a qualifying decision for the averaging and readout algorithms. The Taylor approximation is only valid for small $\partial I/\partial t$ values.

3. Nonpulsatile Applications a. Valsalva's Maneuver to Simulate Pulsatile Case

It is interesting to see the similarities between this AC pulsatile derivation and an analogous DC technique. By taking the logarithm of two intensity ratios, values of $\epsilon_b$ and $\epsilon_i$ can be obtained from the modified Beer-Lambert equation (equation (2a)). These same extinction coefficients can be manipulated by the identical proportionality constants $R_1$ and $R_2$ found previously to exactly eliminate $\epsilon_{i1310}X_i$ and yield $$\frac{\epsilon_{b805}}{\epsilon_{b1310}} = \frac{U_{805}}{U_{1310} - R_2(U_{970} - R_1 U_{805})} \quad (19)$$

Where the term $$U_\lambda = \ln\left(\frac{I_2}{I_1}\right)_\lambda$$

represents the logarithm of intensity ratios at $X_b$ values of $X_1$ and $X_2$.

It should also be noted that the two derivations (AC and DC) fold into one another through the power series expansion of the $\ln(1+Z)$ function:

$$\ln(1+Z) = Z - \frac{Z^2}{2} + \frac{Z^3}{3} - \ldots \quad (20)$$

When the value $\Delta I = I_2 - I_1$, it can be seen that $$\ln\left(\frac{I_2}{I_1}\right) = \ln\left(\frac{\Delta I + I_1}{I_1}\right) = \ln\left(1 + \frac{\Delta I}{I_1}\right) \quad (21)$$

$$= \frac{\Delta I}{I} + \text{High Order Terms}$$

which means that for small changes in $X_b$, the AC (partial derivative) and DC (logarithmic) derivations are similar and can each be-precisely compensated through this differential-ratiometric technique to provide an noninvasive $\epsilon_{b805}/\epsilon_{b1310}$ ratio which is independent of both the constant and time-varying tissue and interstitial fluid terms.

One currently preferred method of obtaining the two intensity ratios is to have the patient perform Valsalva's maneuver. Valsalva's maneuver is an attempt to forcibly exhale with the glottis, nose, and mouth closed. This maneuver increases intrathoracic pressure, slows the pulse, decreases return of blood to the heart, and increases venous pressure obtaining intensity measurements before and during Valsalva's maneuver provide sufficiently different intensity ratios to utilize equation (19). Even a deep breath can be enough to obtain sufficiently different intensity ratios.

b. Stepper Motor Technique

Another technique to simulate pulsatile blood flow and to eliminate the skin's optical scattering effects, while at the same time preserving the blood-borne hematocrit and oxygen saturation information, is described below. By utilizing a stepper motor 9 in the earlobe clip assembly 10 on an earlobe 11 of a patient, such as that illustrated in FIGS. 5, 5A, 14, and 15, one can produce a variation of $X_b$ sufficient to utilize equation 19. The stepper motor 9 could even produce a bloodless ($X_b=0$) state, if required. However, equation 19 shows that only a difference between $X_{b1}$ and $X_{b2}$ is needed.

The major advantage of this technique is that under clinical conditions of poor blood flow, poor blood pressure, or peripheral vascular disease, where pulse wave forms are of poor quality for the $(\partial I/\partial t)/I$ technique, this DC-stepper motor technique could be utilized.

C. Oxygen Saturation Determination

The above techniques describe conditions and equations wherein isobestic wavelengths are chosen such that the hematocrit value obtained has no interference from oxygen saturation, hence an independently determined hematocrit value.

One, however, may choose $\lambda_2$ (the reference wavelength) in equation (13) at 1550 nm as well. In the radiation region 900 to 2000 nm the blood absorption coefficients depend on hematocrit and water, whereas at 805 nm the blood absorption coefficient only depends on hematocrit. Therefore, utilizing in combination, wavelengths of 660, 805, and 1550 will also give a technique to determine hematocrit ($\epsilon_{805}/\epsilon_{1550}$) and oxygen saturation ($\epsilon_{660}/\epsilon_{805}$)

These 3 wavelengths are particularly important since 660, 805, and 1550 nm (or 1310 nm) are readily available LEDs, such as, respectively, MLED76-Motorola, HLP30RGB-Hitachi, and ETX1550-EPITAXX (or NDL5300-NEC), with the benefits of low cost and low optical power (reducing any question of possible eye damage).

The manufacturing of a multi-chip LED emitter becomes reasonable, cost-wise, and provides increased accuracy since the LED sources have practically no separation distances and appear as a single point source.

This invention may be applied to the determination of other components (included, but not limited to, glucose, or cholesterol) in any range of the electromagnetic spectrum in which spectrophotometric techniques can be utilized.

4. Currently Preferred Apparatus

Figure 1A:
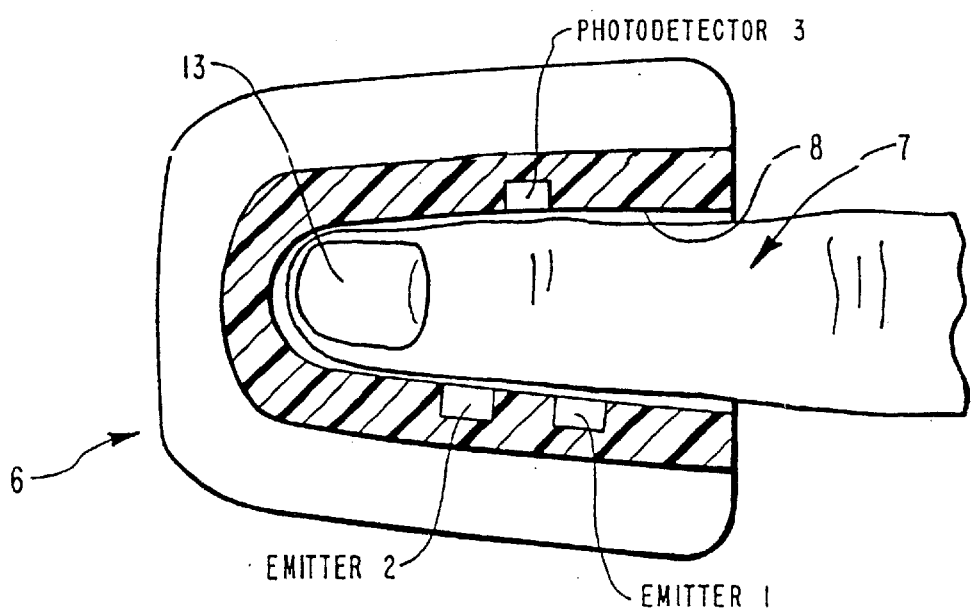
FIG. 1A is an enlarged cross sectional view of the body part (finger) and system components represented in FIG. 1 used in a transmission mode.

An earlobe clip assembly 10 as in FIGS. 5, 5A, 14, and 15 (with or without the stepper motor 9 shown in FIG. 6A) and a finger clip assembly 6 used on a finger 7 of a patient as shown in FIGS. 1, 1A, and 1B, are two currently preferred embodiments for practicing the present invention. The photodiodes 3 and emitters 1 and 2 in each are placed in accordance with appropriate alignment.

Consider first the sensor technology in the transmissive mode of operation. An earlobe or fingertip housing can be provided with discreet emitters and two photodiode chips (of different sensitivity ranges, 600–1000 nm and 1000–1700 nm ranges) placed on one substrate, such as a TO-5 can (Hamamatsu K1713-03). The emitters likewise can be two or more emitter chips (i.e., $\lambda$=805, 1310, 660, and 950 nm) placed on a common substrate and illuminated through a TO-39 can.

Finally, a single substrate multi-wavelength emitter and a multi-wavelength detector, assembled in one small physical housing for each, make alignment and detection sensitivity more repeatable, and hence-more accurate.

The preferred emitter chips would have wavelengths, for hematocrit-only measurements, at 805 nm, 950 nm, and 1310 nm (or 805 nm, 950 nm, and 1550 nm). Although in theory, an emitter having a wavelength of 970 nanometers, rather than 950 nm, would provide more accurate information, 970 nm emitters are not presently available commercially. These wavelengths are currently preferred because of the different curvature and baseline offset of the $\epsilon$ versus Hematocrit at those wavelengths. See FIG. 16. Hence, the hematocrit information will exist in the ratio $\epsilon_{\lambda 1}/\epsilon_{\lambda 12}$. See FIG. 3.

Furthermore, the choice of 805 nm and 1310 nm (or 1550 nm) rather than 570 nm and 805 nm is because there is no water absorption in the 570 nm (or 589 nm) and 805 nm isobestic wavelengths. However, there is tremendous water absorption at 1310 nm and 1550 nm. Hence, the ratio of 570 nm to 805 nm, as a reference, would not yield hematocrit information because there would be no offset due to water in the plasma. See FIGS. 12A and 12B and FIGS. 13A and 13B.

If hematocrit-independent oxygen saturation is desired then the emitter chip wavelengths would be 660 nm, 805 nm, 950 nm, and 1310 nm (or 1550 nm) (the 660 nm is MLED76, Motorola or TOLD 9200, Toshiba). Likewise, the photodetector single substrate could house at least two chips, such as a Hamamatsu K1713-03.

It will be appreciated that those skilled in the art would be able to add other chips to the single substrate at wavelengths sensitive to other metabolites (glucose, cholesterol, etc.). The above mentioned emitter and detector connections can be seen in the analog schematic diagram illustrated in FIGS. 6 and 8B–8D.

The sensor technology in the reflectance mode must conform to two embodiment parameters. See FIG. 1B. The diameter and thickness of the aperture 8 of finger clip assembly 6 in which finger 7 is received in combination with the sensor-emitter separation distances are important to provide a detection region within the subdermis 12 at points a and b of FIG. 1B, where the radiation impinges on blood-tissue without the multiple scattering effects of the epithelial layer, $R_r$. The determination of optimum sensor 3 separation and aperture 8 sizes is done empirically from numerous finger 7 with varying callous and fingernails 13. Minimum sensor separation and aperture diameters can be established wherein $R_r$ of equation (14) is eliminated.

Figure 6:
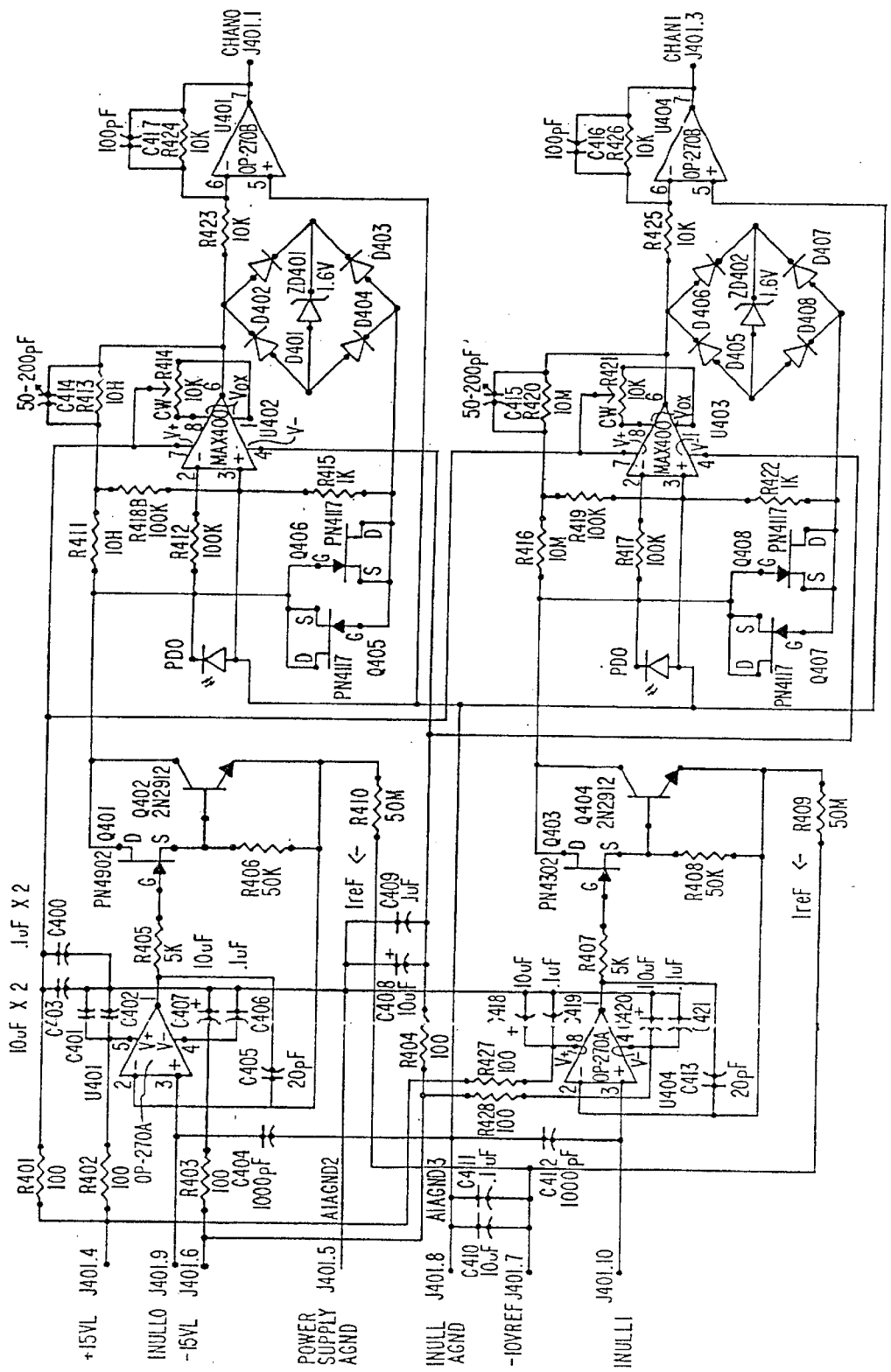
FIG. 6 provides a detailed schematic diagram of the low level sensor circuitry included in the presently preferred system of the present invention.
Figure 7A:
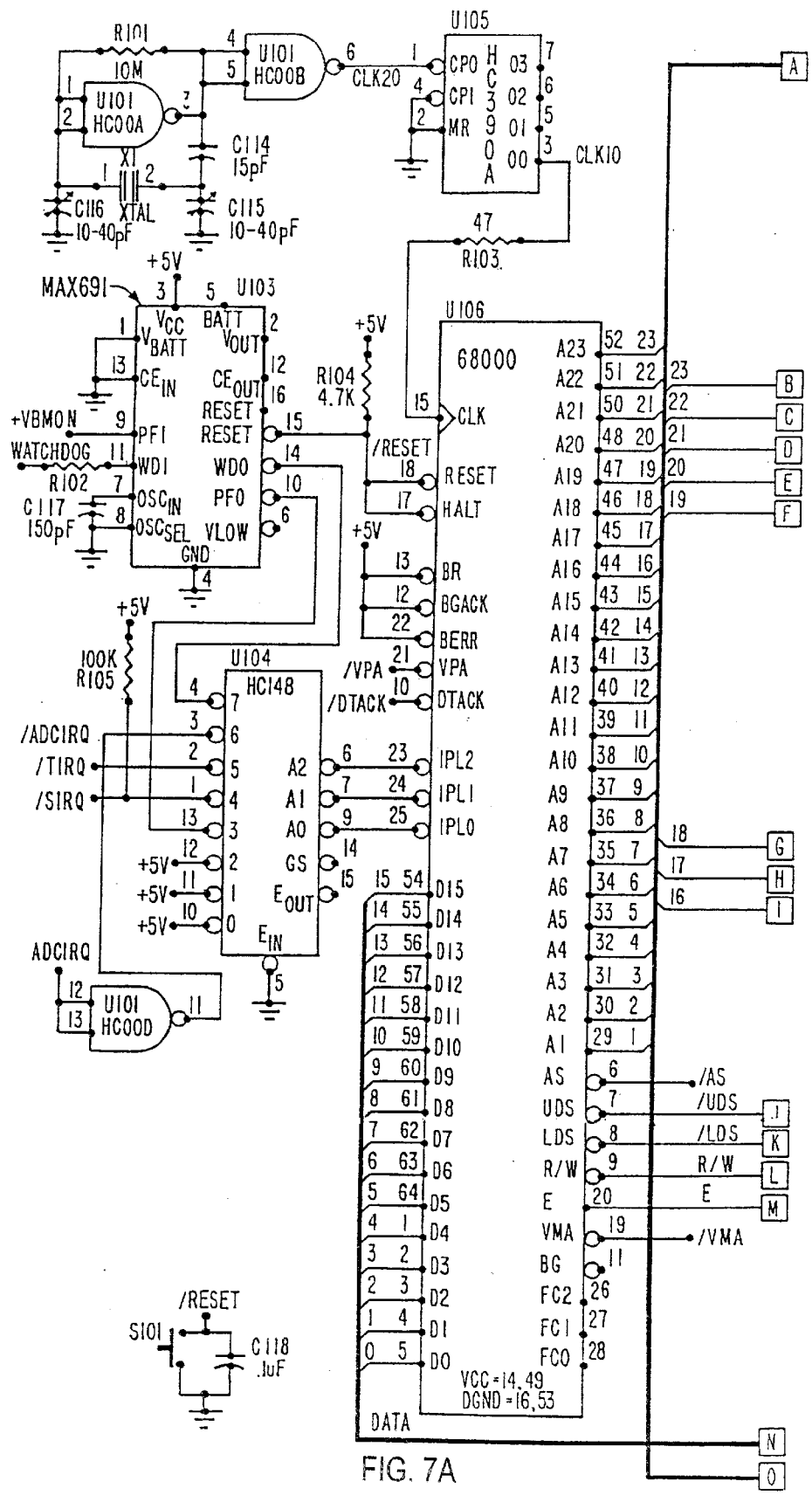
Figure 7B:
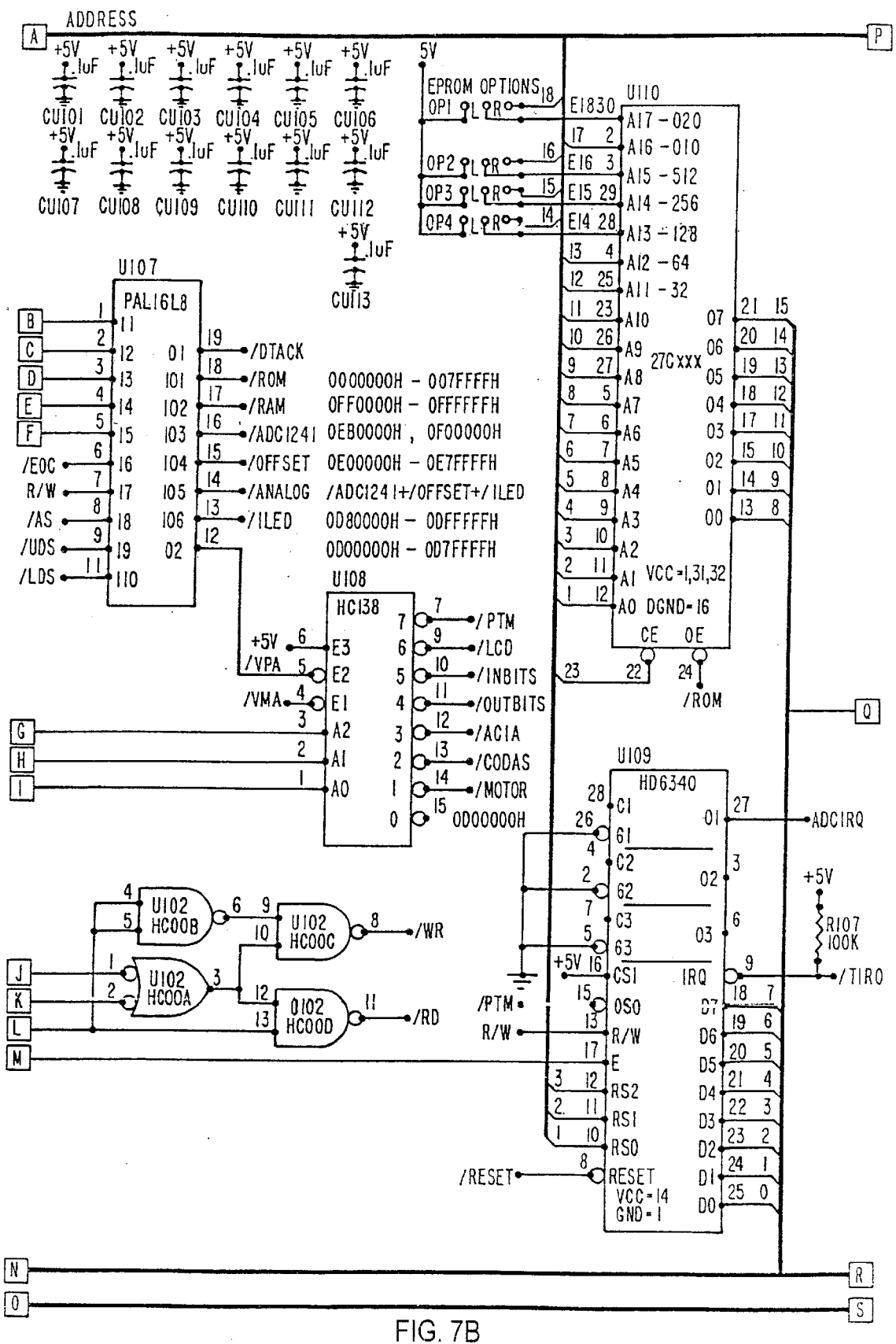
Figure 8A:
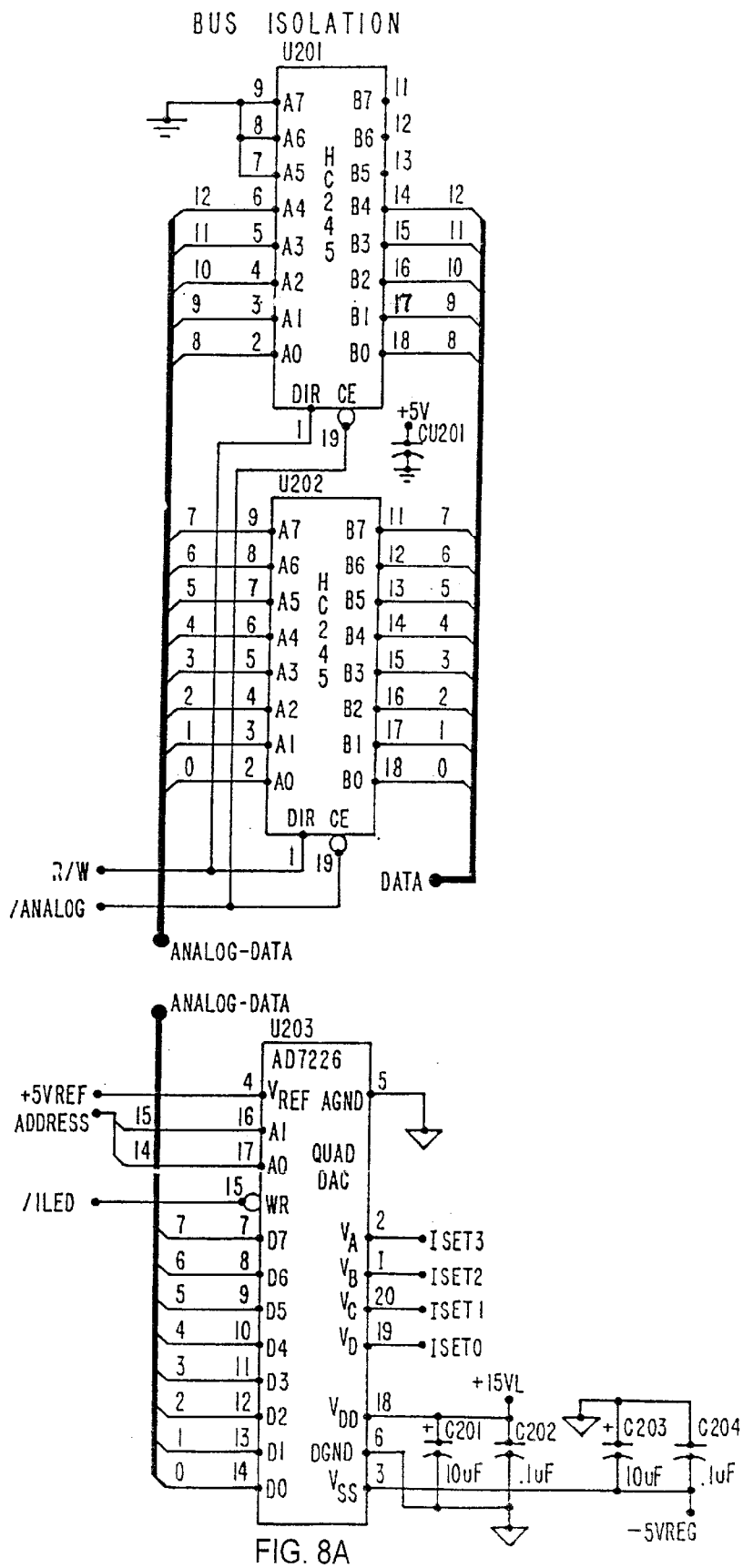
Figure 8C:
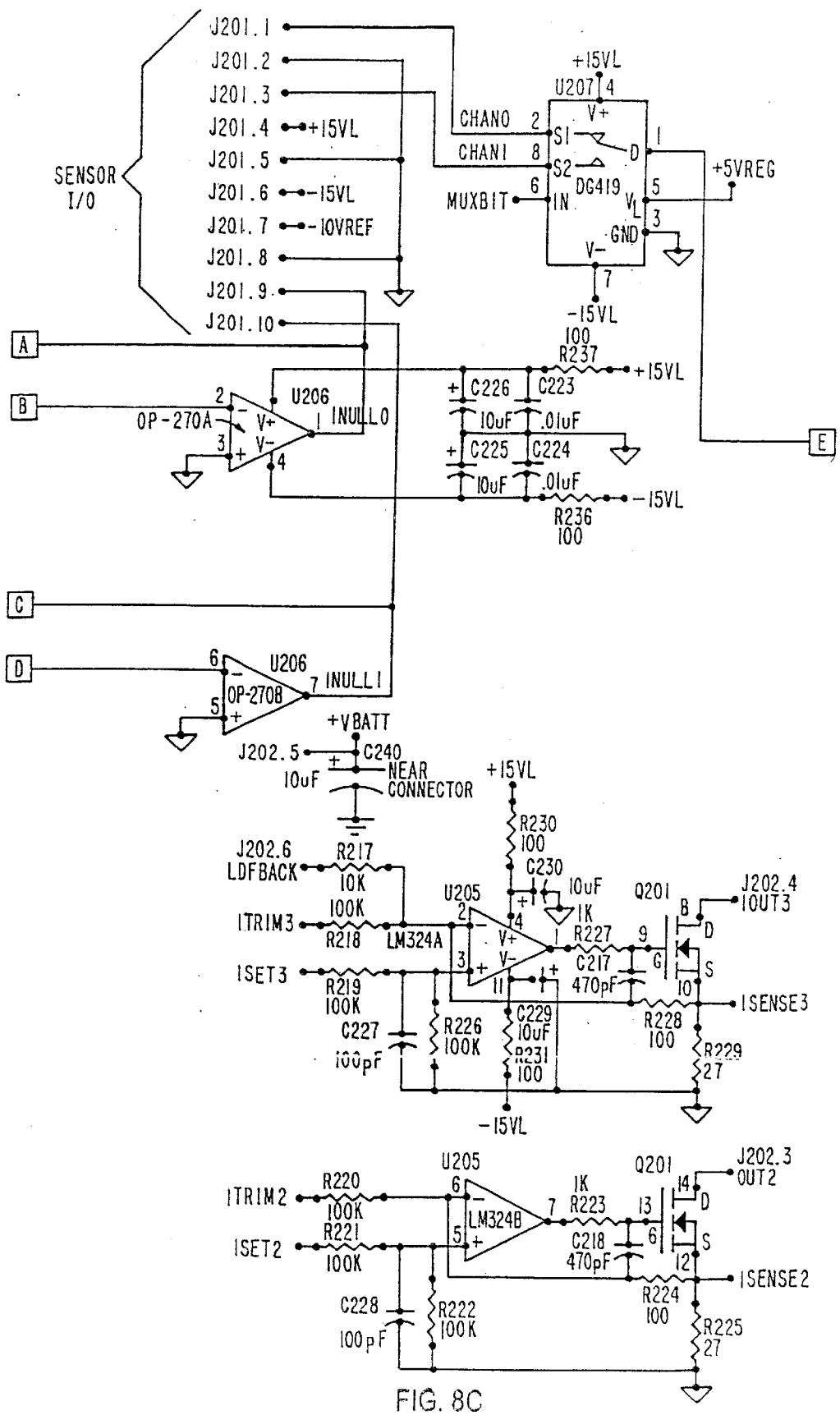
Figure 8D:
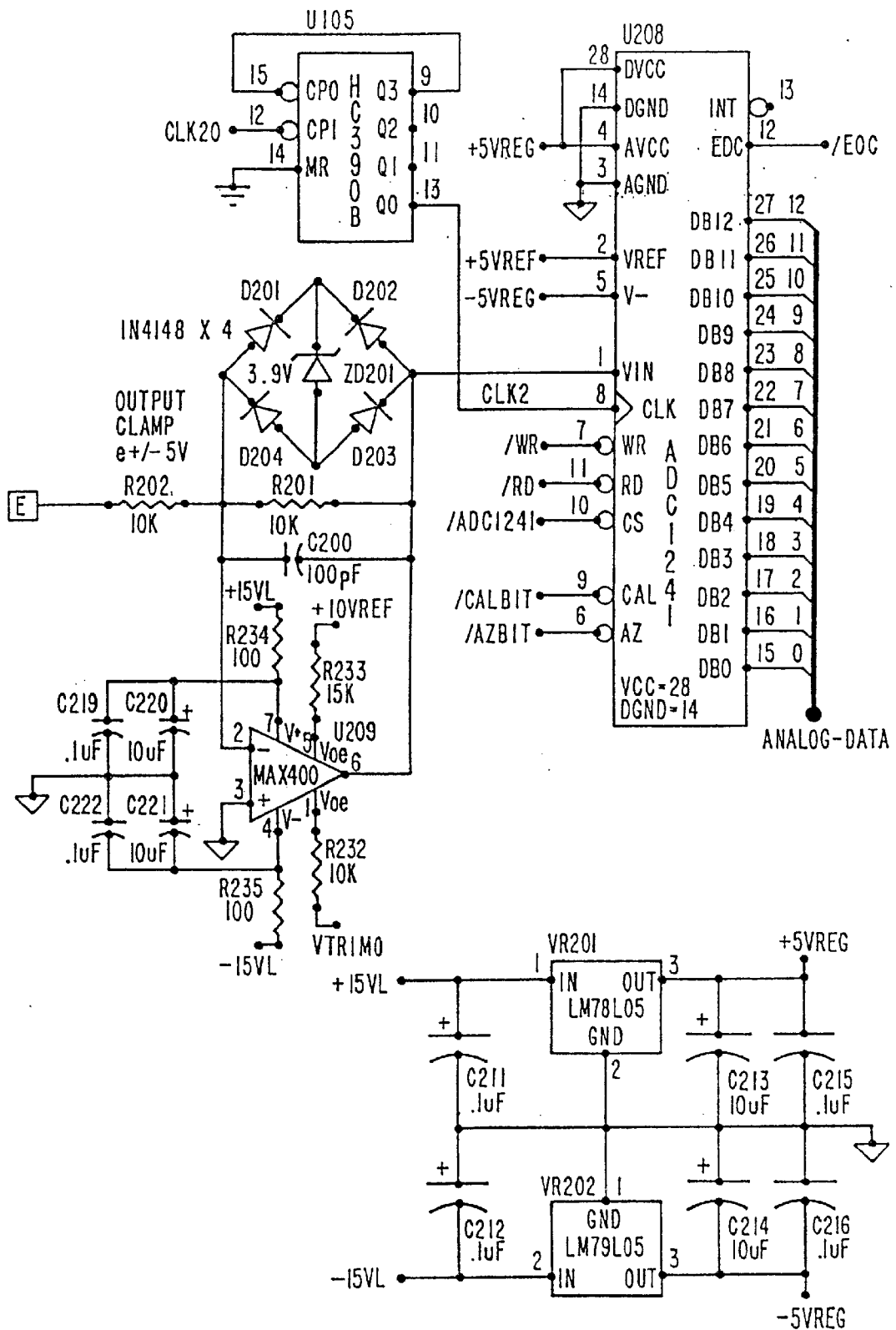
Figure 9A:
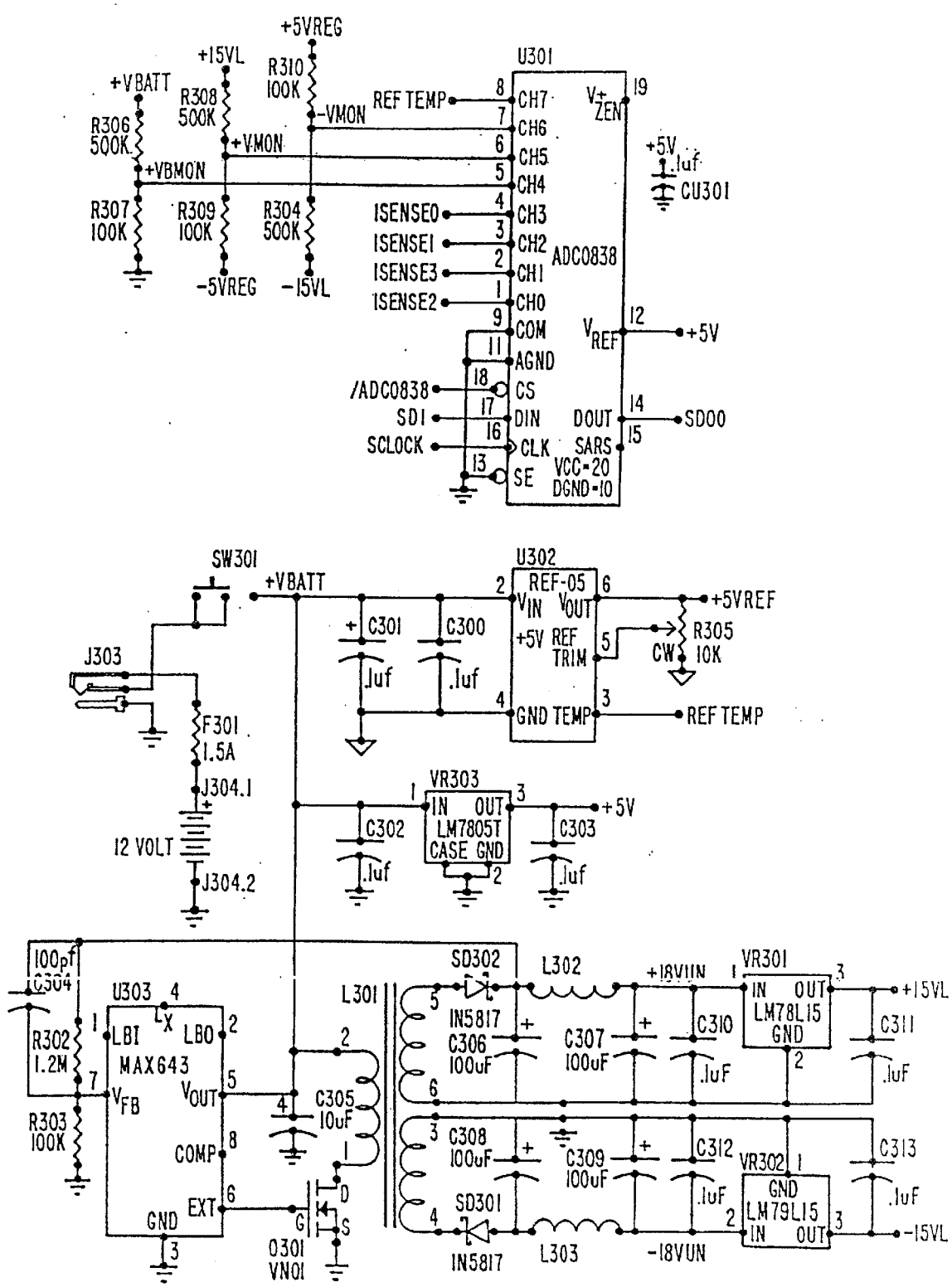
FIGS. 9A–9C provide a detailed schematic diagram of the power supply and input/output (I/O) section included in the presently preferred system of the present invention.
Figure 9B:
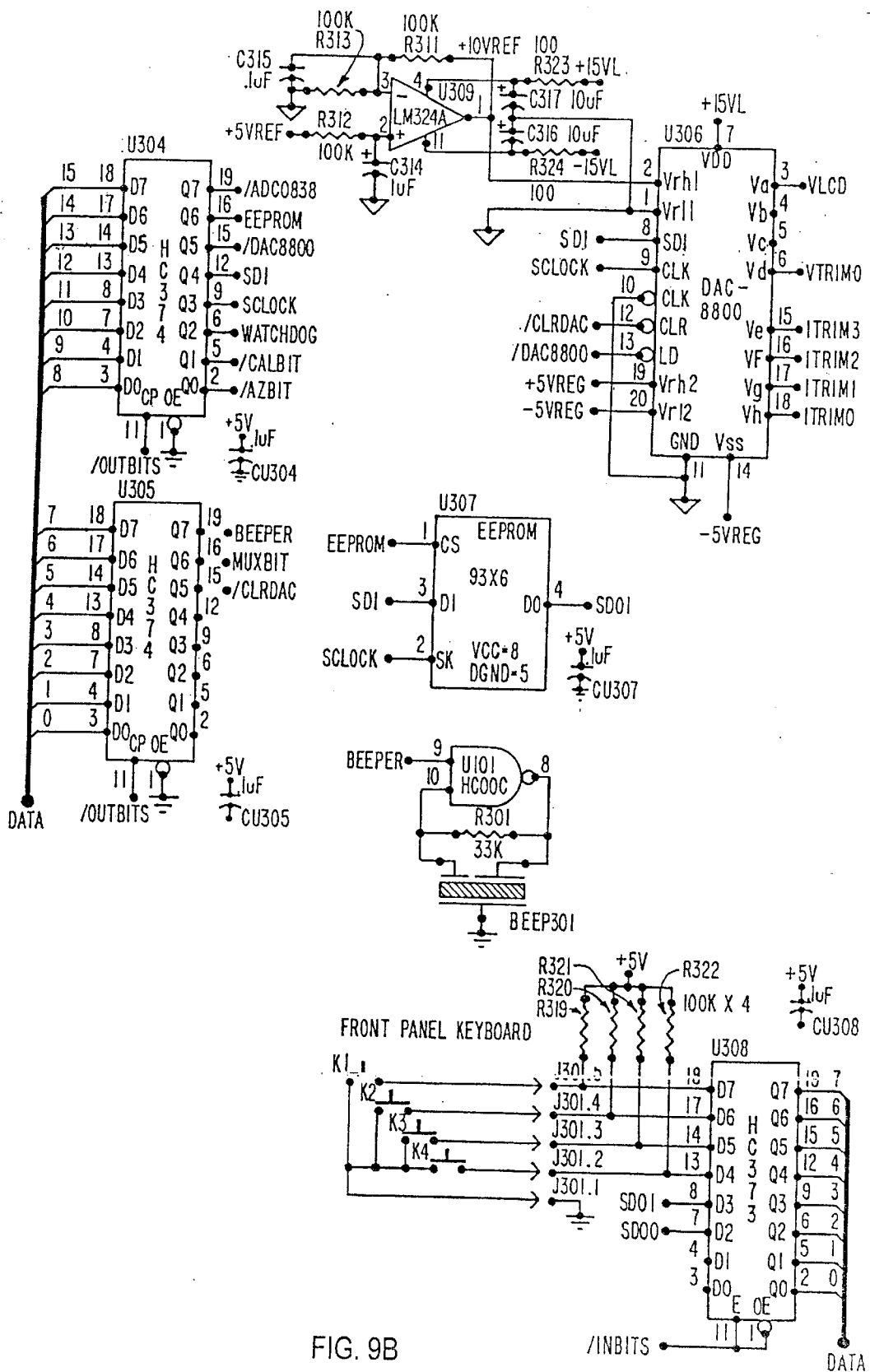
Figure 9C:
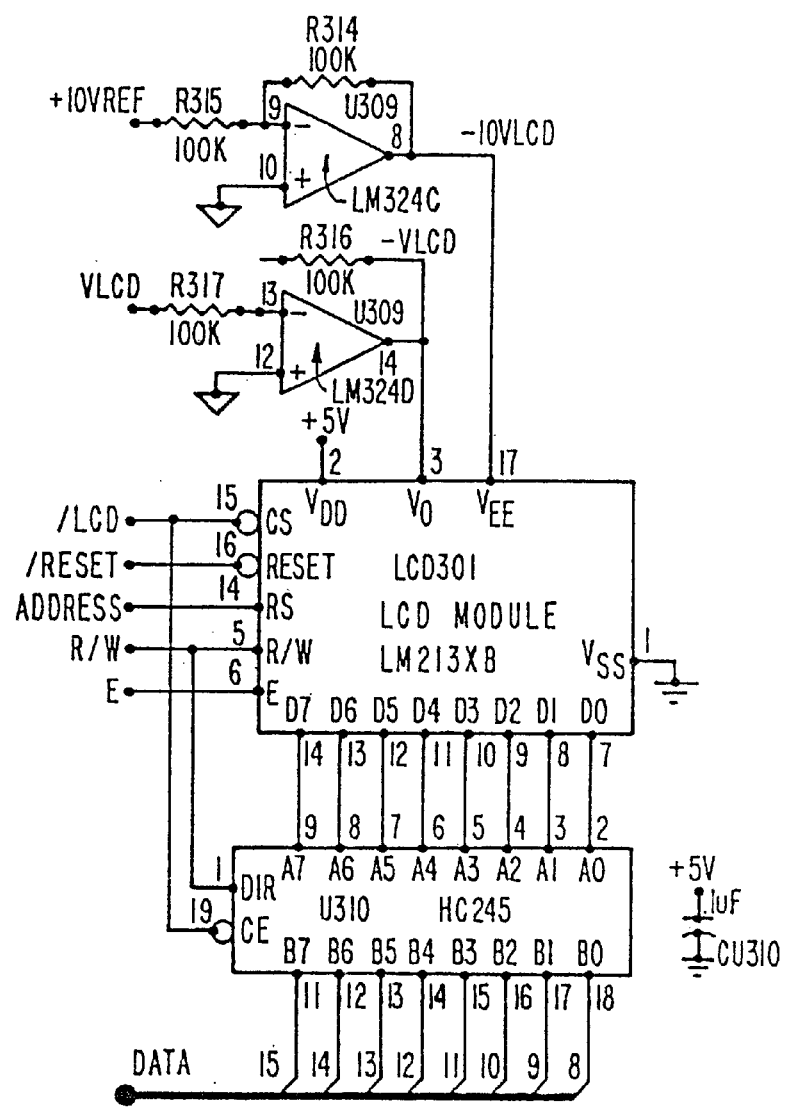

FIGS. 6, 7A–7C, 8A–8D, and 9A–9B detail the electronics of one circuit suitable for use within the scope of the present invention. The memory and computation means (FIGS. 7A–7C) are connected via a "bus" structure between PROMS (U110,U111), microprocessor MC68HC000 (U106), static RAMS (U112,U113), and isolation buffers to the low-level analog circuitry (FIG. 6). A crystal controlled oscillator circuit (U101A,B) is divided by 2 to provides a symmetric master clock to the microprocessor; this clock is further subdivided and used to provide clocking for the analog-to-digital converter0 (U208) and timer (U109). Strobe lines are generated through a decoder arrangement to drive each of the subsystems of the device and also control the isolation bus buffers (U201,U202).

Timer outputs are fed back into the microprocessor and encoded (U104) to produce interrupts at specific intervals for system functions. One timer is shared by subsystems which control the liquid crystal display means, the keyboard entry means, the audible indicator, and the cycling background system self-test. Another timer is dedicated exclusively to provide a high priority interrupt to the microprocessor; this interrupt drives software which controls the basic sensor sampling mechanism. An expansion connector (J101) is included to allow extended testing of the device or connection to external data-logging equipment such as a printer or computer interface.

The local bus isolates the sensitive analog circuitry from the main digital circuitry. This prevents spurious crosstalk from digital signals into the analog circuitry and thereby reduces superimposed noise on the measured signals. It is on this local bus that the Digital-to-Analog Converters (DAC) and Analog-to-Digital Convertors (ADC) transmit and receive digital information while processing the low-level analog signals.

The Low Level Sensor electronic section, FIG. 6, combines subsystems to both measure and modulate the current produced from each optical sensor. Since a pulsatile component of the optical energy transmitted through or reflected off of tissue comprises only a small part of the overall optical energy incident on the sensor, means are provided to "null out" in a carefully controlled and accurately known way the non-pulsatile component of the light-produced current in the sensing detector. The remaining signal can then be dc-amplified and filtered in a straightforward manner and presented to the ADC (U208) for conversion into a digital value representative of the relative AC pulsatile component. Furthermore, because the relationship between the nulling current and the average value of this AC component is known, the DC component can easily be calculated as a function of the sensing means' sensitivities and the electronic stages' gains. The functions determining these AC and DC values can (if necessary) be trimmed in software by calibration constants which sire stored in EEPROM (U307) and retrieved each time the unit is powered on.

The current which modulates the optical sources (LEDs or laser diodes) is also controlled (U203) and precisely adjusted (U306) to optimize signal reception and detection. Through software control, the modulation current can be adjusted on a pulse-by-pulse basis to minimize noise-induced inaccuracies. Furthermore, by sampling the sensors with the modulation sources disabled appropriately, background noise (such as 60 Hz) can be rejected digitally as common-mode noise. Thus, by controlling the optical source energy and modulating the nulling current in the photosensor circuitry, it is possible to effectively cancel the effects of ambient radiation levels and accurately measure both the static (DC) and time-varying (AC) components of transmitted or reflected light.

Interrupt-driven software algorithms acquire the sensor data, provide a real-time pulse wave contour, and determine pulse boundaries. Completed buffers (i.e. one entire pulse per buffer) of sensor data are then passed to the foreground software processes for computation. This involves the determination of the background-compensated AC pulsatile and DC static values of intensities for each wavelength. Through averaging and selective elimination of abnormal values, results are then calculated using equation (9) and displayed on the LCD. The modulating and nulling currents are (if necessary) also adjusted to utilize the electronic hardware efficiently and optimally.

5. Summary

Although the foregoing discussion has related to noninvasive analysis of blood hematocrit information, it will be appreciated that the above-mentioned emitters, sensors, and circuitry may be adapted for invasive in vitro analysis of blood hematocrit values. The principles within the scope of the present invention which compensate for spatial, geometric, and tissue variations may be used to compensate for similar variations in an in vitro blood container. Such a device would allow hematocrit values to be determined rapidly and accurately.

Those skilled in the art will also appreciate that the methods within the scope of the present invention for determining blood hematocrit values may be adapted for determining non-hematocrit biologic constituent values such as glucose, cholesterol, etc. To determine biologic constituent information, the effects of competing blood, tissue, and interstitial fluid constituents must be eliminated. It is believed that these effects may be eliminated by appropriate modification of the differential ratiometric techniques described above.

It is important to recognize that the present invention is not directed to determining the tissue hematocrit value. The tissue hematocrit value, in contrast with the blood hematocrit value, reflects the amount of red blood cells in a given volume of tissue (blood, interstitial fluids, fat, hair follicles, etc.). The present invention is capable of determining actual intravascular blood hematocrit and hemoglobin values.

From the foregoing, it will be appreciated that the present invention provides a system and method for noninvasively and quantitatively determining a subject's hematocrit or other blood constituent value. The present invention determines the hematocrit noninvasively by utilizing electromagnetic radiation as the transcutaneous information carrier. Importantly, the present invention may be used on various body parts to provide accurate quantitative hematocrit values.

It will also be appreciated that the present invention also provides a system and method which can provide immediate and continuous hematocrit information for a subject. The present invention further provides a system and method for noninvasively determining a subjects's blood oxygen saturation ($S_aO_2$) independent of the subject's hematocrit. In addition, the present invention provides a system and method for noninvasively determining a subject's hematocrit and/or blood oxygen saturation even under conditions of low blood perfusion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for determining hematocrit of blood of a patient, the blood flowing in a pulsatile fashion in a body part of the patient or in an extracorporeal passageway in communication with the circulatory system of the patient so as to be subjectable to transcutaneous examination in the body part or to noninvasive examination in the extracorporeal passageway, the body part and the extracorporeal passageway defining a blood conduit and the method comprising the steps of:

(a) selecting a first radiation wavelength that is isobestic for Hb and $HbO_2$ and not extinguished by non-hemoglobin components of the blood;

(b) selecting a second radiation wavelength that is isobestic for Hb and $HbO_2$ and extinguished by non-hemoglobin components of the blood;

(c) directing the first radiation wavelength into the blood conduit;

(d) directing the second radiation wavelength into the blood conduit;

(e) detecting the amount of steady state component of the first wavelength extinguished after passing through the blood conduit;

(f) detecting the amount of steady state component of the second wavelength extinguished after passing through the blood conduit;

(g) detecting the amount of pulsatile component of the first wavelength;

(h) detecting the amount of pulsatile component of the second wavelength;

(i) determining a ratio of the pulsatile component of the first wavelength to the steady state component of the first wavelength;

(j) determining a ratio of the pulsatile component of the second wavelength to the steady state component of the second wavelength;

(k) obtaining a mean value for the ratio of the pulsatile component of the first wavelength to the steady state component of the first wavelength over a period of time;

(l) obtaining a mean value for the ratio of the pulsatile component of the second wavelength to the steady state component of the second wavelength over a period of time; and (m) determining the hematocrit by the ratio of the mean values obtained for the first and second wavelengths.

2. The method for determining the hematocrit of the blood of a patient of claim 1, further comprising the steps of:

(n) displaying the hematocrit.

3. The method for determining the hematocrit of the blood of a patient of claim 1, further comprising the steps of:

(n) selecting a third radiation wavelength;

(o) directing the third radiation wavelength into the blood conduit;

(p) determining a mean value for a ratio of pulsatile component of the third wavelength to steady state component of the third wavelength over a period of time; and (q) calculating a corrected hematocrit value using a linear combination of the first, second and third wavelengths and their ratios.

4. The method for determining the hematocrit of the blood of a patient of claim 3, further comprising the steps of:

(r) display the corrected hematocrit value.

5. A system for determining hematocrit of blood of a patient, the blood flowing in a pulsatile fashion in a body part of the patient or in an extracorporeal passageway in communication with the circulatory system of the patient so as to be subjectable to transcutaneous examination in the body part or to noninvasive examination in the extracorporeal passageway, the body part and the extracorporeal passageway defining a blood conduit, the system comprising:

(a) blood conduit receiving means for receiving a blood conduit containing the flowing blood of the patient;

(b) a first emitter positioned on said conduit receiving means for emitting a first radiation wavelength that is isobestic for Hb and $HbO_2$ and not extinguished by non-hemoglobin components of the blood;

(c) a second emitter positioned on said conduit receiving means for emitting a second radiation wavelength that is isobestic for Hb and $HbO_2$ and extinguished by non-hemoglobin components of the blood;

(d) means for directing the first radiation wavelength into the blood conduit;

(e) means for directing the second radiation wavelength into the blood conduit;

(f) means for detecting the amount of steady state component of the first wavelength extinguish after passing through the blood conduit;

(g) means for detecting the amount of steady state component of the second wavelength extinguished after passing through the blood conduit;

(h) means for detecting the amount of pulsatile component of the first wavelength;

(i) means for detecting the amount of pulsatile component of the second wavelength;

(j) means for determining a ratio of the pulsatile component of the first wavelength to the steady state component of the first wavelength;

(k) means for determining a ratio of the pulsatile component of the second wavelength to the steady state component of the second wavelength;

(l) means for obtaining a mean value for the ratio of the pulsatile component of the first wavelength to the steady state component of the first wavelength over a period of time;

(m) means for obtaining a mean value for the ratio of the pulsatile component of the second wavelength to the steady state component of the second wavelength over a period of time; and (n) means for determining the hematocrit by the ratio of the mean values obtained for the first and second wavelengths.

6. The system for determining the hematocrit of the blood of a patient of claim 5, further comprising:

(o) means for displaying the hematocrit.

7. The system for determining the hematocrit of the blood of a patient of claim 5, further comprising:

(o) a third emitter positioned on said conduit receiving means for emitting a third radiation wavelength;

(p) means for directing the third radiation wavelength into the blood conduit;

(q) means for determining a mean value for a ratio of pulsatile component of the third wavelength to steady state component of the third wavelength over a period of time; and (r) means for calculating a corrected hematocrit value using a linear combination of the first, second and third wavelengths and their ratios.

8. The system for determining the hematocrit of the blood of a patient of claim 7, further comprising:

(s) means for display the corrected hematocrit value.

\* \* \* \* \*